United States Patent [19]
Berger et al.

[11] 3,966,743
[45] June 29, 1976

[54] ORTHO FUSED CYCLOALKANO-4-QUINOLONE-3-CARBOXYLIC ACID DERIVATIVES

[75] Inventors: Herbert Berger, Mannheim-Kafertal; Alfred Rhomberg, Mannheim-Neuostheim; Kurt Stach, Mannheim-Waldhof; Wolfgang Vömel, Mannheim; Winfriede Sauer, Mannheim-Wallstadt, all of Germany

[73] Assignee: Boehringer Mannheim G.m.b.H., Mannheim, Germany

[22] Filed: Sept. 9, 1974

[21] Appl. No.: 504,589

Related U.S. Application Data

[63] Continuation-in-part of Ser. Nos. 363,211, May 23, 1973, abandoned, Ser. No. 363,235, May 23, 1973, abandoned, and Ser. No. 326,203, Jan. 24, 1973, abandoned, said Ser. No. 363,211, is a continuation of Ser. No. 98,957, Dec. 16, 1970, abandoned, which is a continuation-in-part of Ser. No. 843,182, July 18, 1969, abandoned, Ser. No. 363,235, , which is a continuation of Ser. No. 119,035, Feb. 25, 1971, abandoned.

[30] Foreign Application Priority Data

| July 23, 1968 | Germany | 1770951 |
| Mar. 14, 1969 | Germany | 1912944 |
| Mar. 13, 1970 | Germany | 2011885 |
| May 25, 1970 | Germany | 2025363 |
| Sept. 4, 1970 | Germany | 2043817 |
| Feb. 19, 1972 | Germany | 2207856 |

[52] U.S. Cl. .................. 260/287 CF; 260/286 R; 260/471 A; 424/258
[51] Int. Cl.² .................................. C07D 215/56
[58] Field of Search .......... 260/287 R, 283 S, 286 R

[56] References Cited
UNITED STATES PATENTS

| 2,966,489 | 12/1960 | Hepworth et al. | 260/287 R |
| 3,287,458 | 11/1968 | Kaminsky et al. | 260/287 R |
| 3,324,135 | 6/1967 | Lesher | 260/287 R |
| 3,506,667 | 4/1970 | Kaminsky | 260/287 R |
| 3,524,858 | 8/1970 | Kaminsky et al. | 260/287 R |

FOREIGN PATENTS OR APPLICATIONS

| 2,054,503 | 4/1971 | France | 210/287 |
| 1,770,951 | 7/1972 | Germany | |
| 1,912,944 | 10/1970 | Germany | |
| 2,011,885 | 9/1971 | Germany | |
| 2,025,363 | 12/1971 | Germany | |
| 1,210,638 | 10/1970 | United Kingdom | 260/288 |

*Primary Examiner*—Alton D. Rollins
*Assistant Examiner*—David E. Wheeler
*Attorney, Agent, or Firm*—Burgess, Dinklage & Sprung

[57] ABSTRACT

Cycloalkano-quinolone derivatives having antimicrobial activity characterized by the formula:

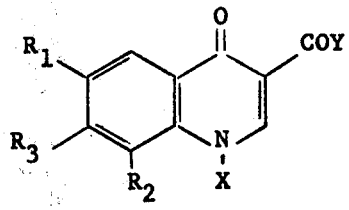

wherein one of $R_1$ and $R_2$ designates hydrogen, halogen, nitro, amino, hydroxyl, acylamino, acyloxy, alkoxy or aryloxy and the other taken together with $R_3$ forms an akylene bridge containing 2 to 6 carbon atoms, X is hydrogen, lower alkyl, which may be substituted by a member of the group consisting of halogen, hydroxyl, acyloxy, alkoxy, aryloxy, aralkyloxy, mercapto, alkylmercapto, arylmercapto, arylsulfonyl, and alkylsulfonyl, or X is unsubstituted alkenyl including alkadienyl, or alkynyl and Y is hydroxyl, amino or lower alkoxy, and the pharmaceutically acceptable salts thereof.

36 Claims, No Drawings

ORTHO FUSED CYCLOALKANO-4-QUINOLONE-3-CARBOXYLIC ACID DERIVATIVES

The instant application is a continuation-in-part of Ser. No. 363,211 filed May 23, 1973, now abandoned, Ser. No. 363,235 filed May 23, 1973, now abandoned, and Ser. No. 326,203 filed Jan. 24, 1973, now abandoned; and, inasmuch as it contains only subject matter disclosed in said prior cases, may be conveniently regarded as a consolidation of said prior applications. Said Ser. No. 363,211 is itself a continuation of Ser. No. 98,957 filed Dec. 16, 1970, now abandoned which, in turn, is a continuation-in-part of Ser. No. 843,182 filed July 18, 1969, now abandoned; and Ser. No. 363,235 is a continuation of Ser. No. 119,035 filed Feb. 25, 1971 now abandoned.

This invention relates to cycloalkano-quinolone derivatives and is especially concerned with compounds of the foregoing type which have been found to be effective as antimicrobial agents. More particularly, this invention relates to various cycloalkano-quinolone derivatives and salts thereof, therapeutic compositions containing the same useful in the treatment of urinary tract infections and to a method for the treatment of such conditions.

In accordance with the present invention, there has now been discovered and synthesized a new group of compounds all possessing the following formula:

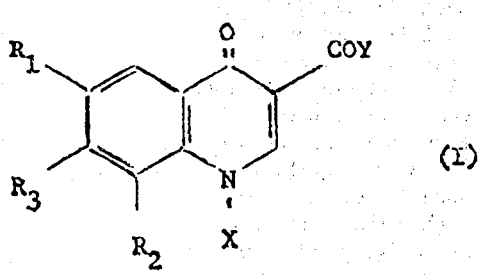

(I)

wherein one of $R_1$ and $R_2$ represents a member selected from the group consisting of hydrogen, chlorine, nitro, amino, alkanoylamino of from 1 to 5 carbon atoms, and the other of $R_1$ and $R_2$ taken together with $R_3$ forms an alkylene bridge of from 3 to 5 carbon atoms, X is hydrogen or lower alkyl of from 1 to 6 carbon atoms, which may be substituted by a member of the group consisting of halogen, alkanoyloxy of from 1 to 5 carbon atoms, alkoxy, hydroxyl, phenyloxy, alkylmercapto, tosylsulfonyl and alkylsulfonyl the alkyl moieties of said members being of from 1 to 6 carbon atoms, or X is unsubstituted alkenyl of from 2 to 6 carbon atoms and 1 to 2 double bonds, or alkynyl of up to 6 carbon atoms and one triple bond, and Y is a member selected from the group consisting of hydroxyl, amino and alkoxy of from 1 to 6 carbon atoms; and pharmacologically acceptable salts thereof.

In a more specific embodiment of this invention, there are provided compounds of the formula

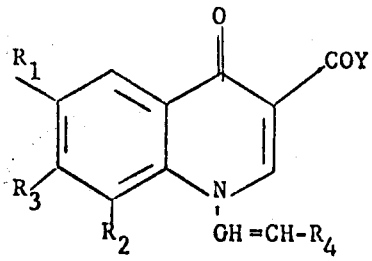

wherein
one of the symbols $R_1$ and $R_2$ is hydrogen and the other one, together with $R_3$, represents a 1,3-propylene bridge;
$R_4$ is hydrogen or lower alkyl; and
Y is hydroxyl, lower alkoxy, or substituted or unsubstituted amino;
and the pharmacologically compatible salts thereof. Furthermore, the invention provides, in another specific embodiment, compounds of the formula

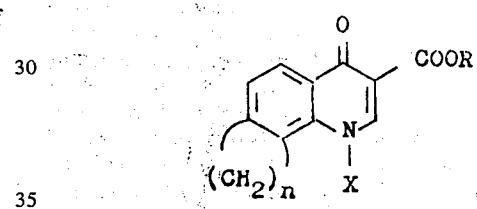

wherein R is lower alkyl; X is lower alkyl or substituted lower alkyl wherein the substituent is at least one member selected from chlorine, hydroxy, lower alkoxy, lower alkanoyloxy, lower alkylthio, lower alkylsulfonyloxy and lower aryl sulfonyloxy; or X is lower alkenyl; and $n$ is 3, 4 or 5.

Another aspect of the present invention is concerned with the use of these cycloalkano-quinolone derivatives and with the pharmaceutical compositions containing the same in admixture with a solid liquid pharmaceutical carrier or diluent.

The new compounds according to the present invention are characterized by their surprisingly high antimicrobial activity not only in vitro but also in vivo. The new compounds in small concentrations, inhibit the growth of many gram-negative and gram-positive micro-organisms, for example, *Staphylococcus aureus*, *Escherichia coli*, *Proteus vulgaris*, *Streptococcus pyogenes* and *pseudomenas aeruginosa*, the same being known to be causative agents in the production of infections of the urinary tract. As the new compounds according to the present invention are characterized by their marked anti-microbial action in urine, they are outstandingly effective in the treatment of infections of the urinary tract.

The novel cycloalkano-quinolone derivatives according to the present invention can be prepared by the cyclization of cycloalkano-benzene derivatives having the formula:

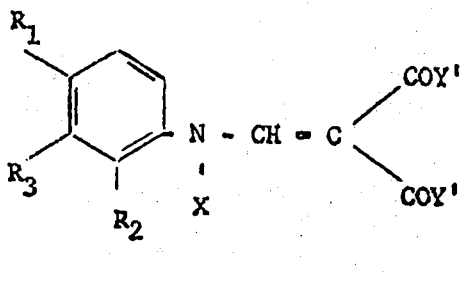

(II)

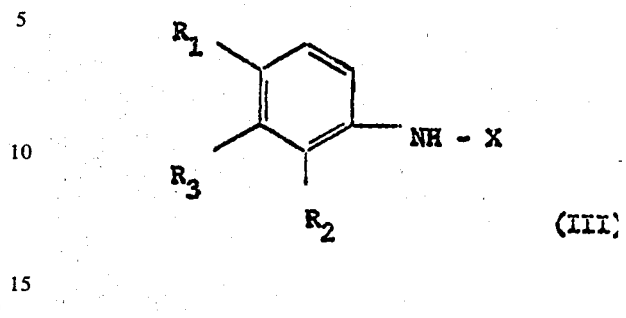

(III)

wherein $R_1$, $R_2$, $R_3$ and X have the same significance as given above, and Y' is amino or alkoxy. Thereafter, if desired, the compounds of formula (I) which are obtained can be saponified, esterified, transesterified or amidated in any order and/or the substituents $R_1$ and/or $R_2$ introduced or chemically changed and/or when X is hydrogen, the compounds can be N-alkylated and/or if X is alkenyl or alkynyl it can be isomerized and/or if X is a substituted alkyl, said substituted can be chemically changed and/or if Y is hydroxyl or $R_1$ and/or $R_2$ is amino, the compounds can be converted into their pharmacologically compatible salts by reaction thereof with an inorganic or organic base or acid, respectively.

The cyclization of the compounds (II) to cycloalkanoquinolone derivatives (I), in which Y is alkoxy, is preferably carried out under the conditions of the Gould-Jacobs reaction in an inert solvent, for example "Dowtherm" (a high boiling point solvent available from Dow Chemical Co.), diethyl phthalate, diphenyl ether or mineral oil at a temperature of 220°–280°C, preferably of about 250°C. However, it is also possible to carry out the cyclization using therefor an agent capable of splitting off the elements of water or of an alkanol, for example, using concentrated sulfuric acid or phosphorus oxychloride.

The introduction of the substituents $R_1$ and/or $R_2$ can take place before or after the cyclization and is generally carried out in the conventional manner; for example, nitro groups are introduced by reaction with a nitration mixture, halogen atoms by direct halogenation and amino groups indirectly via the corresponding diazonium salts. By reaction of the nitro groups introduced, which can be carried out either catalytically, for example in the presence of Raney nickel, or with a strong reducing agent, such as sodium dithionite, amino groups are formed which can easily be acylated or can be converted into the diazonium salt which can then be hydrolyzed to give the corresponding hydroxy compound. By alkylation or acylation of the hydroxyl group, there is obtained the corresponding ether or ester, respectively.

The compounds (II) which are used as starting materials can be prepared by the reaction of a compound having the formula:

wherein $R_1$, $R_2$, $R_3$ and X have the same meanings as set out above, with a malonic acid ester derivative of the formula:

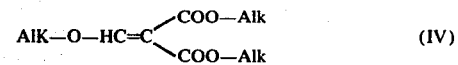

(IV)

wherein Alk is alkyl, followed, if desired, by reaction with ammonia.

The conversion of the compounds (I), in which Y is a hydroxyl group, into pharmacologically compatible salts takes place in the conventional manner, for example, by neutralization with a non-toxic inorganic base such as sodium hydroxide, potassium hydroxide, sodium carbonate, potassium carbonate, sodium bicarbonate, potassium bicarbonate and the like or pharmaceutically acceptable amines such as monoalkylamines, dialkylamines, mono-, di- and tri- alkanolamines for instance triethylamine, monoethanolamine and the like. Compounds (I) in which $R_1$ and/or $R_2$ are amino can be neutralized with a non-toxic inorganic or organic acid such as hydrochloric acid, sulfuric acid, formic acid, acetic acid, citric acid, phosphoric acid, maleic acid, etc.

The saponification of compounds (I), in which Y is lower alkoxy or amino, takes place in the conventional manner under use of aqueous acids or bases, whereby in the latter case, the salts according to the present invention can be obtained directly.

The esterification of compounds (I), in which Y is hydroxyl, can be carried out under dehydrating conditions with the use of an excess of an appropriate alcohol. The dehydration of the reaction mixture can be achieved either by azeotropic distillation with a solvent serving as entraining agent, for example, with methylene chloride or benzene, or by the addition of a dehydrating agent as for example, concentrated sulfuric acid, hydrogen chloride or boron trifluoride etherate. In some cases, the hydroxyl group Y can also be alkylated by reaction with a diazoalkane.

The transesterification of compounds (I), wherein Y is alkoxy, is carried out in an excess of the anhydrous alcohol to be introduced as the ester component with the addition of catalytic amounts of mineral acid, for example, of hydrogen chloride or concentrated sulfuric acid.

Compounds (I), in which Y is alkoxy, can easily be converted into the corresponding amides by reaction with ammonia.

For the N-alkylation of compounds (I), wherein X is hydrogen, these can be advantageously used, alkyl halides, sulfates or tosylates, the reaction preferably being carried out in a comparatively high boiling solvent, such as dimethyl sulfoxide or dimethyl formamide.

Some substituted N-alkyl compounds are advantageously prepared by chemically changing said substituent afterwards.

An N-hydroxy-alkyl group can be acylated with a reactive acid derivative. Especially preferred acid derivatives are the acid anhydrides and acid halides. The reaction proceeds best in inert solvents with the addition of a weak base.

An N-hydroxy-alkyl group may further be changed into halogen by the reaction with hydrogen halogenide, the water being formed is advantageously removed by azeotropic distillation.

Stronger alkylating agents, as the alkyl-chlorides and alkylsulfonates change N-hydroxy-alkyl and N-mercapto-alkyl groups into N-alkoxy-alkyl and N-alkylmercapto-alkyl groups.

The hydrolysis of N-alkoxy-alkyl or N-aralkoxy-alkyl substituents is possible in the absence of other hydrolizable substituents ($R_1$, $R_2$, Y), by boiling in concentrated halogen hydracid without attacking of the cycloalkanochinolone system. An N-halogenalkyl group may be changed into an N-alkylmercaptoalkyl or N-arylmercaptoalkyl group through the reaction with an alkali salt of the corresponding mercaptan.

Oxidation of the alkylmercaptoalkyl derivatives leads to the corresponding alkylsulfonylalkyl derivatives; potassium permanganate or hydrogen peroxide may be used as oxidizing agents. N-alkynyl substituents can be isomerized to the allenyl-substituents by heating in strong alkaline solutions as aqueous sodium hydroxide to yield compounds which are otherwise difficult to prepare.

For the rearrangement (isomerisation) of the N-allyl-quinolones, they are preferably heated with an aqueous alkali, for example, with an aqueous solution of sodium hydroxide, or with a strong organic base, optionally with the addition of solubilizing agents, for example, alcohols, cyclic ethers, dimethyl sulfoxide or the like.

If the N-allyl-quinolones are prepared from quinolones and allyl esters of strong acids with the addition of acid-binding agents, such as a weak alkali or tertiary amine, then, after the addition of stronger bases and subsequent boiling, the rearrangement can be carried out directly in the same vessel without intermediate isolation of the N-allyl-quinolone. In the case of allyl-quinolones which only rearrange with difficulty, the reaction can be accelerated with sodium alcoholates in alcohol or dimethyl sulfoxide.

In the case of the condensation of compounds of formula

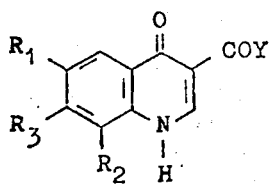

and formula

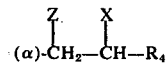

in which $R_4$ has the same meaning as above and X' and Z individually represent reactive radicals or together represent an oxygen or sulfur atom, with the splitting off of Z and of the amine hydrogen atom and subsequently elimination of X' and one of the α-hydrogen atoms.

It is recommended to use different active residues for the groups Z and X' in order to ensure that the condensation proceeds are in the right direction. Z is thereby preferably a halogen atom, especially an iodine or bromine atom, or a sulfonic acid residue, whereas X' represents a bromine or chlorine atom or a hydroxyl group which can possibly be blocked by a residue which is easily split off. Condensation takes place under alkaline conditions, for example, with the addition of tertiary amines, which are able to bind the liberated acid HZ. If the group X' is also the residue of an acid, splitting off thereof can also take place under these conditions. If X' is a hydroxyl group or a derivative thereof which is not split off under alkaline conditions, then this group can be eliminated with water-binding acidic agents, for example, sulfuric acid or phosphorus pentoxide, with the formation of the vinyl double bond.

The following Examples are given for the purpose of illustrating the present invention but are in no way to be construed as limiting the scope thereof.

EXAMPLE 1

1,4-dihydro-3-carbethoxy-cyclopentano(h)-quinolone-(4)

2.5 g ethyl α-carbethoxy-β-(4-indanyl-amino)-acrylate were introduced in portions into 50 ml diphenyl ether which had previously been heated to 250°C. The reaction mixture thereby obtained was stirred for 15 minutes at 250°C, then rapidly cooled and mixed with ligroin. The precipitate which was formed was filtered off and washed with ligroin. There was obtained 1.95 g 1,4-dihydro-3-carbethoxy-cyclopentano(h)-quinolone-(4) which melted, with decomposition, at 285°C.

The ethyl αcarbethoxy-β-(4-indanyl-amino)-acrylate used as starting material was prepared by reacting 1.7 g 4-amino-indan with 3 g diethyl ethoxymethylenemalonate in 3 ml boiling benzene. After stripping off the volatile components under vacuum, there were obtained 3.7 g ethyl α-carbethoxy-β-(4-indanyl-amino)-acrylate (m.p. 25°–30°C) which could be used without further purification.

EXAMPLE 2

1-ethyl-1,4-dihydro-3-carboxy-cyclopentano(h)-quinolone-(4)

Variant A:

1.3 g 1,4-dihydro-3-carbethoxy-cyclopentano(h)-quinolone-(4) which had been prepared by the procedure described in Example 1, were stirred together with 2.1 g potassium carbonate, 3.9 g ethyl iodide and 12.5 ml dimethyl formamide, for 2 hours at 100°C and the reaction mixture thereafter evaporated to dryness under vacuum. The residue was heated under reflux for 15 minutes in 10 ml 2N sodium hydroxide solution, cooled, diluted with 10 ml water and extracted with ethyl acetate. The aqueous phase was extracted with animal charcoal for a few minutes at 20°C and, after filtration, weakly acidified (pH 2–3) with 5N hydrochloric acid. The 1-ethyl-1,4-dihydro-3-carboxy-cyclopentano(h)-quinolone-(4) which was separated out was washed with water and dried, to give 0.75 g of product which, following recrystallization from dimethyl formamide, melted at 260°–261°C.

VARIANT B:

30 g 1,4-dihydro-3-carbethoxy-cyclopentano(h)-quinolone-(4) which had been prepared by the procedure described in Example 1, was heated under reflux, while stirring, for one hour with 185 ml dioxan and 120 ml of a concentrated aqueous solution of sodium hydroxide. After cooling, 60 ml water and 60 ml dioxan were added to the reaction mixture and then with efficient stirring, 144 g diethyl sulfate were introduced over the course of 4 hours at 50°C. The reaction mixture was allowed to cool, water was added thereto until a clear solution was obtained and this was then acidified, while cooling, to a pH of 1–2, by the addition of concentrated hydrochloric acid. The 1-ethyl-1,4-dihydro-3-carboxy-cyclopentano-(h)-quinolone-(4) which was then separated out was filtered off, washed with water and dried to give 27.7 g of crude product which, following recrystallization from dimethyl formamide, melted at 270°–271°C.

VARIANT C:

7.95 g 1,4-dihydro-3-carboxy-cyclopentano-(h)-quinolone, prepared according to the method described in Example 13, which follows, were suspended in 40 ml concentrated sodium hydroxide solution and 60 ml dioxan and 48 g diethyl sulfate added dropwise thereto at 50°C, under stirring and over a period of 4 hours. The reaction mixture was then cooled, diluted with water until a clear solution was obtained and thereafter acidified with concentrated hydrochloric acid. The 1-ethyl-1,4-dihydro-3-carboxy-cyclopentano(h)-quinolone-(4) which was separated out was filtered off, washed with water and dried to give 8.9 g of product which, after recrystallization from dimethyl formamide, had a melting point of 270°–272°C.

EXAMPLE 3

1,4-dihydro-3-carbethoxy-cyclopentano(g)-quinolone-(4)

5.0 g ethyl α-carbethoxy-β-(5-indanyl-amino)-acrylate were introduced portionwise into 100 g diphenyl ether which had previously been heated to 250°C and the mixture heated for a further 15 minutes at 250°C. The resultant mixture was then stirred for 15 minutes at 250°C, cooled rapidly and mixed with ligroin. The precipitate which was obtained was filtered off and washed with ligroin. There were obtained 3.85 g 1,4-dihydro-3-carbethoxy-cyclopentano(g)-quinolone-(4) which melted, with decomposition, at 286°C.

The ethyl α-carbethoxy-β-(5-indanyl-amino)-acrylate used as starting material was prepared by reacting 3 g 5-amino-indan with 5.3 g diethyl ethoxymethylene-malonate in 6 ml boiling benzene. After stripping off the volatile components under vacuum, there were obtained 6.8 g ethyl α-carbethoxy-β-(5-indanyl-amino)-acrylate which had a melting point of 25°–30°C and which could be used without any further purification.

EXAMPLE 4

1-ethyl-1,4-dihydro-3-carboxy-cyclopentano(g)-quinolone-(4)

2.57 g 1,4-dihydro-3-carbethoxy-cyclopentano(g)-quinolone-(4) which had been prepared by the method described in Example 3, were stirred together with 4.2 g potassium carbonate, 7.8 g ethyl iodide and 25 ml dimethyl formamide, for 2 hours at 100°C and subsequently evaporated to dryness under vacuum. The residue was refluxed for 15 minutes with 10 ml 2N sodium hydroxide solution, then cooled, diluted with 10 ml water and extracted with ethyl acetate. The aqueous phase was treated for a few minutes with animal charcoal at 20°C and, after filtration, weakly acidified (pH 2–3) with 5N hydrochloric acid. The 1-ethyl-1,4-dihydro-3-carboxy-cyclopentano(g)-quinolone-(4) which separated out was washed with water and dried to give 2.2 g of product which, after recrystallization from dimethyl formamide, had a melting point of 290°C.

EXAMPLE 5

Mixture of 1,4-dihydro-3-carbethoxy-cyclopentano(g)- and (h)-quinolone-(4)

10 g of a mixture of ethyl α-carbethoxy-β-(5-indanyl-amino)-acrylate and ethyl α-carbethoxy-β-(4-indanyl-amino)-acrylate (weight ratio about 3:2) were introduced rapidly and in portions into 50 g diethyl phthalate which had previously been heated to 280°C. During the introduction, the temperature was carefully maintained at 280°C. The resulting reaction mixture was then immediately cooled, mixed with ether, the precipitate obtained filtered off and washed with ether. There were thusly obtained 4.6 g of a mixture of 1,4-dihydro-3-carbethoxy-cyclopentano(g)- and (h)-quinolone-(4) which melted with decomposition at 260°–262°C.

The ester mixture used as starting material was obtained by boiling under reflux for 2 hours 7.2 g of a isomeric mixture of 5-amino-indane and 4-amino-indane (prepared by the nitration of indane with a nitration mixture at 0°C followed by catalytic reduction of the isomeric nitro-indane mixture obtained by the nitration) and 12.8 g diethyl ethoxy-methylene-malonate in 15 ml benzene and subsequent stripping off of the volatile components under vacuum. There were obtained 16 g of an oily isomeric mixture.

EXAMPLE 6

Mixture of 1-ethyl-1,4-dihydro-3-carboxy-cyclopentano(g)- and (h)-quinolone-(4)

3.85 g of a mixture of 1,4-dihydro-3-carbethoxy-cyclopentano(g)- and (h)-quinolone-(4), prepared by the method described in Example 5, were stirred together with 6.3 g potassium carbonate, 11.7 g ethyl iodide and 38 ml dimethyl formamide, for 2 hours at 100°C and thereafter evaporated to dryness under vacuum. The residue was heated under reflux for 15 minutes with 30 ml 2N potassium hydroxide solution, then cooled, diluted with 10 ml water and extracted with ethyl acetate. The aqueous phase was treated for a few minutes at 20°C with animal charcoal and, following filtration, weakly acidified (pH 2–3) with 5N hydrochloric acid. The mixture of 1-ethyl-1,4-dihydro-3-carboxy-cyclopentano(g)- and (h)-quinolone-(4) which separated out was washed with water and dried to give 2.7 g of product which, after recrystallization from dimethyl formamide, had a melting point of 240°–260°C. The ratio of the two isomers amounted to about 7:6.

EXAMPLE 7

1,4-dihydro-3-carbethoxy-cyclohexano(g)-quinolone-(4)

2.4 g ethyl α-ethoxycarbonyl-β-(1,2,3,4-tetrahydronaphthyl-6-amino)-acrylate were introduced portionwise into 50 ml diphenyl ether which had been previously heated to 250°C. The resulting mixture was stirred for 5 minutes at 250°C, then rapidly cooled and mixed with ligroin. The precipitate which was thereby obtained was filtered off and washed with ligroin. There were recovered 1.21 g 1,4-dihydro-3-carbethoxy-cyclohexano(g)-quinolone-(4) which melted, with decomposition, at 274°–280°C.

The ethyl α-carbethoxy-β-(1,2,3,4-tetrahydronaphthyl-6-amino)-acrylate used as starting material was prepared by the reaction of 2.22 g 6-amino-1,2,3,4-tetrahydronaphthalene with 3.25 g diethyl ethoxy-methylene-malonate in 5 ml boiling benzene. Following stripping off of the volatile components under vacuum, there were obtained 5.1 g of crude product. After trituration of this product with a little isopropanol, followed by filtration there were recovered 3.1 g pure ethyl α-carbethoxy-β-(1,2,3,4-tetrahydronaphthyl-6-amino)-acrylate, which had a melting point of 58°–60°C.

EXAMPLE 8

1,4-dihydro-3-carboxy-cyclohexano(g)-quinolone-(4)

1 g 1,4-dihydro-3-carbethoxy-cyclohexano(g)-quinolone-(4), prepared by the method as set out in Example 7, was heated under reflux for 4 hours in 15 ml 2N potassium hydroxide solution and 5 ml ethanol. The reaction mixture was thereafter diluted with 15 ml water and acidified with hydrochloric acid. The 1,4-dihydro-3-carboxy-cyclohexano(g)-quinolone-(4) which was separated out was filtered off, washed with water and dried. The yield of crude product amounted to 0.8 g. After recrystallization from dimethyl formamide, the compound had a melting point of 274°–276°C.

EXAMPLE 9

1-ethyl-1,4-dihydro-3-carboxy-cyclohexano(g)-quinolone-(4)

1 g 1,4-dihydro-3-carbethoxy-cyclohexano(g)-quinolone-(4), prepared by the method described in Example 7, 9 ml dimethyl formamide, 1.55 g potassium carbonate and 2.88 g ethyl iodide were stirred for 5 hours at 100°C. The resultant reaction mixture was then evaporated under vacuum and the residue obtained heated under reflux for 1 hour with 9 ml 2N sodium hydroxide solution. This reaction mixture was extracted with ethyl acetate and the aqueous phase acidified with hydrochloric acid. The 1-ethyl-1,4-dihydro-3-carboxy-cyclohexano(g)-quinolone-(4) which was then separated out was filtered off, washed with water and dried. After recrystallization from dimethyl formamide, there was obtained 0.65 g of product having a melting point of 262°–266°C.

EXAMPLE 10

1,4-dihydro-3-carbethoxy-cyclohexano(h)-quinolone-(4)

4.35 g ethyl α-carbethoxy-β-(1,2,3,4-tetrahydronaphthyl-5-amino)-acrylate were introduced in portions into 90 ml diphenyl ether which had been previously heated to 250°C. The reaction mixture was then stirred for 5 minutes at 250°C, rapidly cooled and washed with ligroin. There were obtained 3.28 g 1,4-dihydro-3-carbethoxy-cyclohexano(h)-quinolone-(4). The crude product was recrystallized from dimethyl formamide and then melted with decomposition at 274°–275°C.

The ethyl α-carbethoxy-β-(1,2,3,4-tetrahydronaphthyl-5-amino)-acrylate used as starting material was prepared by the reaction of 2.63 g 5-amino-1,2,3,4-tetrahydronaphthalene with 3.87 g diethyl ethoxy-methylene-malonate in 5 ml boiling benzene. Following stripping off of the volatile components under vacuum, there were obtained 5.65 g of crude product which, by trituration with a little isopropanol followed by filtering off of the solvent, yielded 5.1 g pure α-carbethoxy-β-(1,2,3,4-tetrahydronaphthyl-5-amino)-acrylate, which had a melting point of 62°–64°C.

EXAMPLE 11

1,4-dihydro-3-carboxy-cyclohexano(h)-quinolone-(4)

1.0 g 1,4-dihydro-3-carbethoxy-cyclohexano(h)-quinolone-(4), prepared by the method described in Example 10, were boiled under reflux for 4 hours in 15 ml 2N potassium hydroxide solution and 5 ml ethanol. The reaction mixture was then diluted with water and acidified with hydrochloric acid, the 1,4-dihydro-3-carboxy-cyclohexano(h)-quinolone-(4) which was separated out was filtered with suction, washed with water and dried. There were recovered 0.7 g of crude product which, following recrystallization from dimethyl formamide, had a melting point of 280°–283°C.

EXAMPLE 12

1-ethyl-1,4-dihydro-3-carboxy-cyclohexano(h)-quinolone-(4)

1.0 g 1,4-dihydro-3-carbethoxy-cyclohexano(h)-quinolone-(4), prepared according to the procedure described in Example 10, 9 ml dimethyl formamide, 1.55 g potassium carbonate and 2.88 g ethyl iodide were stirred together for 2 hours at 100°C. A further amount of ethyl iodide, diluted with some dimethyl formamide, was then added dropwise at 100°C until a quantitative reaction had occurred, which could be determined chromatographically. Care was taken that the reaction medium remained alkaline during this dropwise addition. This was ensured by the addition of further potassium carbonate where necessary. The reaction mixture was then evaporated under vacuum and the residue heated under reflux for 2 hours with 9 ml 2N sodium hydroxide solution. The resulting reaction mixture was then extracted with ethyl acetate and the aqueous phase acidified with hydrochloric acid. There were thusly obtained 400 mg 1-ethyl-1,4-dihydro-3-carboxy-cyclohexano(h)-quinolone-(4) which, following recrystallization from dimethyl formamide, had a melting point of 223°–225°C.

EXAMPLE 13

1,4-dihydro-3-carboxy-cyclopentano(h)-quinolone-(4)

10 g 1,4-dihydro-3-carbethoxy-cyclopentano(h)-quinolone-(4), prepared by the method described in Example 1, were heated under reflux, while stirring, in 40 ml concentrated aqueous sodium hydroxide solution and 60 ml ethanol. This reaction mixture was then diluted with 50 ml water and acidified with concentrated hydrochloric acid. The 1,4-dihydro-3-carboxy-cyclopentano(h)-quinolone-(4) which was then separated out was filtered off, washed with water and dried. There were obtained 7.95 g of product which melted with decomposition at 280°–281°C. The compound could be recrystallized from dimethyl formamide.

EXAMPLE 14

1-propyl-1,4-dihydro-3-carboxy-cyclopentano(h)-quinolone-(4)

30.9 g 1,4-dihydro-3-carbethoxy-cyclopentano-(h)-quinolone-(4), prepared according to the procedure described in Example 1, were suspended in 600 ml absolute ethanol and 3 g metallic sodium then added to this suspension. After boiling under reflux for 15 minutes, a clear solution was obtained which was evaporated to dryness in a vacuum. The residue was triturated with absolute ether and then filtered off. There were recovered 33 g of residue which, together with 300 ml anhydrous dimethyl formamide, 49 g potassium carbonate and 200 g n-propyl iodide, were heated in an autoclave for 16 hours at 140°C. The contents of the autoclave were thereafter evaporated to dryness under vacuum and the evaporation residue boiled under reflux for 1 hour with 235 ml 2N sodium hydroxide solution. Following cooling, the refluxed material was diluted with 235 ml water, treated with animal charcoal and extracted twice with ethyl acetate. The aqueous phase was adjusted to pH of 2 with concentrated hydrochloric acid, the precipitated carboxylic acid filtered off, washed with water and dried. There were obtained 29.1 g crude 1-propyl-1,4-dihydro-3-carboxy-cyclopentano(h)-quinolone-(4). After recrystallization from dimethyl formamide, the compound had a melting point of 267°–269°C.

EXAMPLE 15

1-n-butyl-1,4-dihydro-3-carboxy-cyclopentano(h)-quinolone-(4)

2.1 g 1,4-dihydro-3-carbethoxy-cyclopentano(h)-quinolone-(4), prepared by the procedure described in Example 1, were suspended in 40 ml absolute ethanol, 0.2 g metallic sodium added thereto and the mixture boiled under reflux for 15 minutes. A clear solution was obtained which was then evaporated to dryness under vacuum. The evaporation residue was triturated with anhydrous ether and filtered off. There were recovered 2.24 g of residue whichm together with 20 ml anhydrous dimethyl formamide, 3.3 g potassium carbonate and 14.7 g n-butyl iodide, were heated in a bomb tube for 16 hours at 140°C. The contents of the bomb tube were then boiled under reflux for 1 hour with 16 ml 2N sodium hydroxide solution. Following cooling, the reaction mixture was diluted with 16 ml water and treated with animal charcoal. After filtering off the animal charcoal, the reaction mixture was extracted with ethyl acetate and the aqueous phase acidified with 5N hydrochloric acid. The 1-n-butyl-1,4-dihydro-3-carboxy-cyclopentano(h)-quinolone-(4), which separated out was filtered off, washed with water and dried. There were obtained 1.55 g of product which, following recrystallization from dimethyl formamide, had a melting point of 218°–219°C.

EXAMPLE 16

1-allyl-1,4-dihydro-3-carboxy-cyclopentano(h)-quinolone-(4)

3.09 g 1,4-dihydro-3-carbethoxy-cyclopentano(h)-quinolone-(4), prepared by the method described in Example 1, were suspended in 60 ml absolute ethanol, 0.3 g metallic sodium was added thereto and the mixture boiled under reflux for 15 minutes. There was obtained a clear solution which was evaporated to dryness under vacuum. There were obtained, following trituration of the evaporation residue with anhydrous ether and filtering, 3.3 g of residue. This residue together with 30 ml anhydrous dimethyl formamide, 5 g potassium carbonate and 4.55 g allyl chloride, were stirred for 4 hours at 100°C. Thereafter, the potassium carbonate was filtered off and the filtrate evaporated to dryness under vacuum. The evaporation residue boiled under reflux for 1 hour with 24 ml 2N sodium hydroxide solution. Thereafter, it was treated with animal charcoal and after filtering off of the charcoal, extracted with ethyl acetate. The aqueous phase was acidified with 5N hydrochloric acid. The 1-allyl-1,4-dihydro-3-carboxy-cyclopentano(h)-quinolone-(4) which separated out was filtered off; washed with water and dried. The yield amounted to 2.6 g. After recrystallization of the crude material from a mixture of dimethyl formamide and dimethyl sulfoxide, the pure compound having a melting point of 250°–253°C was obtained.

EXAMPLE 17

1-isopropyl-1,4-dihydro-3-carboxy-cyclopentano(g)-quinolone-(4)

2.57 g 1,4-dihydro-3-carbethoxy-cyclopentano(g)-quinolone-(4) which had been prepared by the method described in Example 3, were suspended in 10 ml dimethyl formamide, together with 5 g potassium carbonate. Within a period of 2 hours and at a temperature of 100°C, a mixture of 12 g isopropyl iodide and 20 ml dimethyl formamide was added dropwise to the suspension. The reaction mixture was thereafter evaporated in a vacuum and the residue boiled under reflux for 30 minutes with 20 ml 2N sodium hydroxide solution. Following the addition of 20 ml water, the reaction mixture was extracted with ethyl acetate and the aqueous phase acidified with 5N hydrochloric acid. The 1-isopropyl-1,4-dihydro-3-carboxy-cyclopentano(g)-quinolone-(4) which separated out was filtered off, washed with water, dried and thereafter recrystallized from dimethyl formamide. The yield amounted to 380 mg and the product had a melting point of 328°–330°C.

EXAMPLE 18

1-ethyl-1,4-dihydro-3-carboxy-6-nitro-cyclopentano(h)-quinolone-(4)

1.0 g 1-ethyl-1,4-dihydro-3-carboxy-cyclopentano(h)-quinolone-(4), prepared by the procedure which has been described in Example 2, was dissolved in 5 ml concentrated sulfuric acid. The resulting solution was mixed at 20°C with 1 ml 100% nitric acid, stirred for 15 minutes at this temperature and thereafter poured onto ice. The 1-ethyl-1,4-dihydro-3-carboxy-6-nitrocyclopentano(h)-quinolone-(4) which separated out was filtered off, washed with water and dried. There were recovered 968 mg of crude product which was recrystallized from a mixture of 4 parts dioxan and 1 part dimethyl formamide. The pure product melted, with decomposition, at 283°–290°C.

EXAMPLE 19

1-ethyl-1,4-dihydro-3-carboxy-6-amino-cyclopentano(h)-quinolone-(4)

3.0 g 1-ethyl-1,4-dihydro-3-carboxy-6-nitrocyclopentano(h)-quinolone-(4) which had been prepared by the method described in Example 18, were catalytically hydrogenated with hydrogen in dimethyl formamide in the presence of Raney nickel. The crude 1-ethyl-1,4-dihydro-3-carboxy-6-amino-cyclopentano(h)-quinolone-(4) thereby obtained could be recrystallized from glacial acetic acid. Following recrystallization the recrystallized compound had a melting point of 280°–285°C (decomp.). The yield amounted to 1.46 g.

EXAMPLE 20

1-ethyl-1,4-dihydro-3-carboxy-6-N-acetylamino-cyclopentano(h)-quinolone-(4)

VARIANT A:

1.0 g 1-ethyl-1,4-dihydro-3-carboxy-6-aminocyclopentano(h)-quinolone-(4) which had been prepared by the method described in Example 19, was heated under reflux for 30 minutes in 10 ml acetic anhydride. Upon cooling, 1-ethyl-1,4-dihydro-3-carboxy-6-N-acetylamino-cyclopentano(h)-quinolone-(4) separated out and was filtered off, washed with ether, dried and recrystallized from dimethyl formamide. There were recovered 776 mg of product having a melting point of 255°–258°C.

VARIANT B:

3 g 1-ethyl-1,4-dihydro-3-carboxy-6-nitrocyclopentano(h)-quinolone-(4), prepared according to the method described in Example 18, were suspended in a mixture of 30 ml water and 30 ml ethanol and mixed with 40 ml 5N aqueous ammonia solution. 6.0 sodium dithionite were then added thereto in portions over a period of 15 minutes, the temperature of the reaction mixture not being allowed to increase above 40°C. The reaction mixture was thereafter stirred for 15 minutes, concentrated to a considerable extent under vacuum, acidified with 30 ml concentrated hydrochloric acid and evaporated to dryness in a vacuum. The residue was boiled under reflux for 1.5 hours in 50 ml acetic anhydride, filtered while still hot, the filtrate evaporated to dryness and the residue taken up in hot ethanol. Following cooling to 0°C, the 1-ethyl-1,4-dihydro-3-carboxy-6-N-acetylamino-cyclopentano(h)-quinolone-(4) which was formed crystallized out and was filtered off, washed with ethanol, dried and recrystallized from dimethyl formamide to which some acetic anhydride had been added. The yield amounted to 1.43 g and the product had a melting point of 253°–255°C.

EXAMPLE 21

1-[β-Benzyloxyethyl]-1,4-dihydro-3-carboxy-cyclopentano-(h)-quinolone-(4)

2.57 g. 3-carbethoxy-4-hydroxy-cyclopentano-(h)-quinoline, 7 g. potassium carbonate and 830 mg. potassium iodide were suspended in 12 ml. dimethyl formamide and, while stirring at 100°C., a mixture of 13.2 g. 1-iodo-2-benzyloxyethane and 12 ml. dimethyl formamide added dropwise within the course of 7 hours. Inorganic material was removed by hot filtration of the reaction mixture, the residue was then washed with hot dimethyl formamide and the filtrate, together with the washings, was evaporated in a rotary evaporator.

An oily residue was obtained which continued a comparatively large amount of excess 1-iodo-2-benzyloxyethane. This was then distilled off at a pressure of 0.5 mm. Hg. and at a bath temperature of about 160°C. The residue was heated under reflux for 2.5 hours with a mixture of 30 ml. 2N sodium hydroxide solution and 30 ml. ethanol. The alcohol was thereafter evaporated off in a vacuum, the residue mixed with 30 ml. water and 30 ml. ethylene chloride and boiled for about 2–3 minutes. While still hot, the water was separated off in a separating funnel and the ethylene chloride phase extracted three times with 30 ml. amounts of hot water. The aqueous phases were combined and the oily sodium salt of the desired quinolone which precipitated out was brought into solution by heating, whereafter the hot solution was acidified to a pH value of 1–2 with concentrated hydrochloric acid. The precipitated quinolone carboxylic acid was filtered off and boiled out twice with 16 ml. amounts of dioxane. The dioxane extracts were combined and then evaporated to dryness. There were thus obtained 1.1 g. 1-[β-benzyloxyethyl]-1,4-dihydro-3-carboxy-cyclopentano-(h)-quinolone-(4), which had a melting point of 152°–160°C. After recrystallization from alcohol/dioxan, the product had a melting point of 163°–164°C.

EXAMPLE 22

1-[β-Ethoxyethyl]-1,4-dihydro-3-carboxy-cyclopentano-(h)-quinolone-(4)

1.3 g. 3-carbethoxy-4-hydroxy-cyclopentano-(h)-quinolone, 5.25 g. potassium carbonate and 0.5 g. potassium iodide were suspended in 13 ml. dimethyl formamide and, while stirring at 100°–110°C., a mixture of 4.05 g. 1-chloro-2-ethoxyethane and 10.5 ml. dimethyl formamide added dropwise within the course of 7 hours. Inorganic material was removed by hot filtration, the residue was washed with hot dimethyl formamide and the filtrate, together with the washings, was evaporated in a vacuum. The evaporation residue was heated under reflux for half an hour in a mixture of 20 ml. 2N sodium hydroxide solution and 5 ml. dioxan. After cooling, the reaction mixture was acidified with 5N hydrochloric acid and the carboxylic acid which separated out was filtered off and dried. There were obtained 700 mg. crude 1-[β-ethoxyethyl]-1,4-dihydro-3-carboxycyclopentano-(h)-quinolone-(4). After recrystallization from a mixture of dioxan and dimethyl sulfoxide (2:1), there were obtained 350 mg. of pure product, which had a melting point of 159°–160°C.

EXAMPLE 23

1-[β-Phenoxyethyl]-1,4-dihydro-3-carboxy-cyclopentano-(h)-quinolone-(4)

1.3 g. 3-carbethoxy-4hydroxy-cyclopentano-(h)-quinoline, 5.25 g. potassium carbonate and 0.5 g. potassium iodide were suspended in 13 ml. dimethyl formamide and a mixture of 5.8 g. 1-chloro-2-phenoxyethane and 15 ml. dimethyl formamide introduced portionwise, with stirring and at a temperature of 100°–110°C., within a period of 7 hours (about 0.7 ml. of the mixture every 15 minutes). Inorganic material was filtered off with suction from the hot reaction mixture, the residue was washed through with hot dimethyl formamide and the filtrate, together with the washings, were evaporated in a vacuum. The evaporation residue was boiled under reflux for half an hour in a mixture of 20 ml. 2N sodium hydroxide solution and 5 ml. dioxan. After cooling, the reaction mixture was acidified with 5N hydrochloric acid and the 1-[β-phenoxyethyl]-1,4-dihydro-3-carboxy-cyclopentano-(h)-quinolone-(4) which precipitated out was filtered off and dried. The yield was 350 mg. and the compound was obtained in chromatographically pure form. The compound could be recrystallized from dimethyl sulfoxide. It had a melting point of 239°–240°C.

EXAMPLE 24

1-[β-Methoxyethyl]-1,4-dihydro-3-carboxy-cyclopentano-(h)-quinolone-(4)

14.48 g. 3-carbethoxy-4-hydroxy-cyclopentano-(h)-quinolone, 59.2 g. potassium carbonate and 5.64 g. potassium iodide were suspended in 145 ml. dimethyl formamide and a mixture of 40 g. 1-chloro-2-methoxyethane and 128 ml. dimethyl formamide added dropwise, with stirring and at a temperature of 100°–110°C., within the course of 7 hours. Inorganic material was filtered off with suction from the hot reaction mixture, the residue was washed through with hot dimethyl formamide and the filtrate, together with the washings, was evaporated in a vacuum. The evaporation residue was boiled under reflux for half an hour in a mixture of 115 ml. 2N sodium hydroxide solution and 28 ml. dioxan. After cooling, the reaction mixture was acidified with 5N hydrochloric acid to a pH value of 2 and the carboxylic acid which precipitated out was filtered off and dried. There were obtained 7.0 g. 1-[β-methoxyethyl]-1,4-dihydro-3-carboxy-cyclopentano-(h)-quinolone-(4). The compound can be recrystallized from dimethyl sulphoxide, whereafter it had a melting point of 222°–226°C.

EXAMPLE 25

1-[β-Hydroxyethyl]-1,4-dihydro-3-carboxy-cyclopentano-(h)-quinolone-(4)

Variant a:

2.5 g. 1-[β-methoxyethyl]-1,4-dihydro-3-carboxy-cyclopentano-(h)-quinolone-(4) were heated to 100°–110°C. for 1.25 hours with 25 ml. 48% aqueous hydrobromic acid. The reaction mixture was then poured into 125 ml. water, solid material was filtered off with suction and dried. There were obtained 2.2 g. almost pure 1-[β-hydroxyethyl]-1,4-dihydro-3-carboxy-cyclopentano-(h)-quinolone-(4). After recrystallization from a mixture of dioxan and dimethyl formamide, the compound had a melting point of 240°–241°C.

Variant b 1g. 1-[β-benzyloxyethyl]-1,4-dihydro-3-carboxy-cyclopentano-(h)-quinolone-(4) were boiled under reflux for 1.5 hours in 15 ml. concentrated hydrochloric acid. 15 ml. water were then added thereto and the crystals which separated were filtered off with suction. There were obtained 0.71 g. 1-[β-hydroxyethyl]-1,4-dihydro-3-carboxy-cyclopentano-(h)-quinolone-(4), which had a melting point of 233°–235°C.

EXAMPLE 26

1-[β-acetoxy-ethyl]-1,4-dihydro-3-carboxy-cyclopentano-(h)-quinolone-(4)

0.7 g. 1-[β-hydroxyethyl]-1,4-dihydro-3-carboxy-cyclopentano-(h)-quinolone-(4) was boiled under reflux for 1 hour in 8.25 ml. acetyl chloride. Subsequently, excess acetyl chloride was evaporated off and the evaporation residue triturated with water. The solid material was filtered off and boiled out twice with a mixture of benzene and dioxan (1:4). The benzene-dioxan extracts were freed from undissolved components by hot filtration and then evaporated. There was obtained 0.45 g. 1-[β-acetoxy-ethyl]-1,4-dihydro-3-carboxy-cyclopentano-(h)-quinolone-(4) which only contained traces of impurities. After recrystallization from for example, a mixture of dioxan and isopropanol, the compound had a melting point of 180°–186°C., sintering above 170°C.

EXAMPLE 27

1-[β-Tosyloxy-ethyl]-1,4-dihydro-3-carboxy-cyclopentano-(h)-quinolone-(4)

100 mg. 1-[β-hydroxyethyl]-1,4-dihydro-3-carboxy-cyclopentano-(h)-quinolone-(4) were suspended in 2 ml. anhydrous pyridine and 418 mg. p-toluene-sulphonyl chloride added portionwise, while stirring and at ambient temperature, within the course of 20 minutes. Thereafter, the reaction mixture was stirred for a further 45 minutes at ambient temperature, poured on to ice and the solid material filtered off with suction and washed with some isopropanol and ether. After recrystallization from dimethyl formamide, there were obtained 70 mg. 1-[β-tosyloxyethyl]-1,4-dihydro-3-carboxy-cyclopentano-(h)-quinolone-(4), which melts at 237°–238°C. (decomp.).

EXAMPLE 28

1-[β-Chloroethyl]-1,4-dihydro-3-carboxy-cyclopentano-(h)-quinolone-(4)

500 mg. 1-[β-hydroxyethyl]-1,4-dihydro-3-carboxy-cyclopentano-(h)-quinolone-(4) were heated to 140°C. in 10 ml. nitrobenzene and, at the same time, gaseous hydrogen chloride was passed therethrough. The progress of the reaction was followed chromatographically. The reaction was finished when no more starting material was detected in the chromatogram. The water formed during the halogenation reaction must be continuously removed by distillation during the whole course of the reaction. When the reaction was completed, the reaction mixture was diluted with about 50 ml. ligroin, a brown oil thereby separating out. The supernatant ligroin/nitrobenzene solution was decanted off and the oil remaining behind was triturated with isopropanol and crystallized. There were obtained 310 mg. of almost pure 1-[β-chloroethyl]-1,4-dihydro-3-carboxy-cyclopentano-(h)-quinolone-(4). After recrystallization from dimethyl formamide/dioxan (3:7), it had a melting point of 252°–253°C.

EXAMPLE 29

1-[β-Chloroacetoxy)-ethyl]-1,4-dihydroxy-3-carboxy-cyclopentano-(h)-quinolone-(4)

273 mg. 1-[β-hydroxyethyl]-1,4-dihydro-3-carboxy-cyclopentano-(h)-quinolone-(4)- and 3 g. chloroacetyl chloride were heated, while stirring, to 120°C. for 10 minutes. The reaction mixture was then evaporated to dryness and the oily evaporation residue was mixed with ice. Crystallization thereby occurred. The crystals (about 320 mg.) were filtered off with suction, washed with water and thereafter with some isopropanol and subsequently recrystallized from dioxan. There were obtained 200 mg. 1-[β-(chloroacetoxy)-ethyl]1,4-dihydro-3-carboxy-cyclopentano-(h)-quinolone-(4), which had a melting point of 163°–165°C.

EXAMPLE 30

1-[β-Benzoyloxy-ethyl]-1,4-dihydro-3-carboxy-cyclopentano-(h)-quinolone-(4)

75 mg. 1-[β-hydroxyethyl]-1,4-dihydro-3-carboxy-cyclopentano-(h)-quinolone-(4) were dissolved in 1 ml. 5N potassium hydroxide solution, whereafter 100 mg. benzoyl chloride were added, with shaking, at ambient temperature. A white precipitate was formed which was filtered off and triturated with 2N hydrochloric acid. Excess hydrochloric acid was removed by filtration and there were obtained 90 mg. chromatographically pure 1-[β-benzoyloxy-ethyl]-1,4-dihydro-3-carboxy-cyclopentano-(h)-quinolone-(4). After recrystallization from a mixture of dioxan and water (4:1), the compound had a melting point of 221°–222°C.

EXAMPLE 31

1-[β-Methylthio-ethyl]-1,4-dihydro-3-carboxy-cyclopentano-(g)-quinolone-(4)

0.916 g. 3-carboxy-4-hydroxy-cyclopentano-(g)-quinoline, 2.8 g. potassium carbonate and 0.35 g. potassium iodide were suspended in 10 ml. dimethyl formamide and a mixture of 3.16 g. 1-chloro-2-methyl-thioethane in 17 ml. dimethyl formamide were introduced, with stirring and at a temperature of 130°C., within the course of 4 hours. The reaction mixture is further stirred for 45 minutes at 130°C., inorganic material was then filtered off with suction and the filtrate was evaporated to dryness in a vacuum. The evaporation residue was boiled under reflux for 15 minutes in a mixture of 12 ml. 2N sodium hydroxide solution and 3 ml. alcohol, whereafter 15 ml. water were added and the reaction mixture acidified with concentrated hydrochloric acid to a pH value of 1–2. The 1-[β-methyl-thioethyl]-1,4-dihydro-3-carboxy-cyclopentano-(g)-quinolone-(4) which precipitated out, was filtered off and dried. The yield was 1.05 g. The chromatographically almost pure compound can be recrystallized from dimethyl sulphoxide and then had a melting point of 217°–220°C.

EXAMPLE 32

1-[β-Methylsulphonylethyl]-1,4-dihydro-3-carboxy-cyclopentano-(g)-quinolone-(4)

300 mg. 1-[β-methylthioethyl]-1,4-dihydro-3-carboxy-cyclopentano-(g)-quinolone-(4) were boiled for minutes in a mixture of 1 ml. 30% hydrogen peroxide and 4.5 ml. glacial acetic acid. Upon cooling the reaction mixture pure 1-[β-methylsulphonylethyl]-1,4-dihydro-3-carboxy-cyclopentano-(g)-quinolone-(4) crystallized out. This was filtered off and had a melting point of 258°C. (decomp.) The yield was 300 mg.

EXAMPLE 33

1-[β-n-butylthioethyl]-1,4-dihydro-3-carboxy-cyclopentano-(h)-quinolone-(4)

100 mg. 1-β-chloroethyl]-1,4-dihydro-3-carboxy-cyclopentano-(h)-quinolone-(4) were suspended in 1 ml. dioxan and 1 ml. of a 35.3% methanolic solution of sodium butyl mercaptide (prepared from a sodium methanolate solution into which was introduced the stoichiometric amount of n-butyl mercaptan) was added, a clear solution thereby being obtained. The reaction mixture was heated to 60°C. for 2 hours, 3 ml. water were subsequently added thereto and the mixture was extracted with ether and the aqueous phase acidified with 5N hydrochloric acid. The semi-crystalline material obtained was filtered off with suction and triturated with isopropanol. There were thus obtained 50 mg. of chromatographically pure 1-[β-n-butylthioethyl]-1,4-dihydro-3-carboxy-cyclopentano-(h)-quinolone-(4). This compound can be recrystallized from dioxan, whereafter it had a melting point of 180°–182°C.

EXAMPLE 34

1-[β-Ethoxy-ethyl]-1,4-dihydro-3-carboxy-cyclohexano-(g)-quinolone-(4)

0.9 g. 3-carbethoxy-4-hydroxy-cyclohexano-(g) quinoline, 3.5 g. potassium carbonate and 0.35 g. potassium iodide were suspended in 9 ml. dimethyl formamide and a mixture of 2.7 g. 1-chloro-2-ethoxy-ethane and 6.8 ml. dimethyl formamide added dropwise, with stirring and at a temperature of 100°–110°C., with the course of 7 hours. Inorganic material was then filtered off with suction, the residue was washed through with hot dimethyl formamide and the filtrate, together with the washings, was evaporated in a vacuum. The evaporation residue was boiled under reflux for 1 hour in a mixture of 2 ml. 2N sodium hydroxide solution and 1.5 ml. dioxan. After cooling, the reaction mixture was acidified with 5N hydrochloric acid and the carboxylic acid which precipitated out, was filtered off and dried. There were obtained 850 mg. chromatographically pure 1-[β-ethoxy-ethyl]-1,4-dihydro-3-carboxy-cyclohexano-(g)-quinolone which, after recrystallization from dimethyl sulphoxide, had a melting point of 206°–208°C.

EXAMPLE 35

1-[β-Methylthioethyl]-1,4-dihydro-3-carboxy-cyclopentano-(h)-quinolone-(4)

1.0 g. 1-[β-chloroethyl]-1,4-dihydro-3-carboxy-cyclopentano-(h)-quinolone-(4) was suspended in 10 ml. dioxan and a solution of 2.4 g. solid sodium methyl mercaptide in 10 ml. methanol was added thereto.

After stirring the reaction mixture for 2 hours at 60°C., it was cooled, 20 ml. water were added thereto and then it was acidified with 5N hydrochloric acid. The 1-[β-methylthioethyl]-1,4-dihydro-3-carboxy-cyclopentano-(h)-quinolone-(4) which separated out was filtered off and dried. The yield was 950 mg. The product can be recrystallized from dimethyl sulphoxide, whereafter it had a melting point of 288°–230°C.

EXAMPLE 36

1-Methyl-1,4-dihydro-3-carboxy-cyclopentano-(h)-quinolone-(4)

460 mg. metallic sodium were dissolved in 20 ml. hot dimethyl sulphoxide. After cooling, 2.57 g. 3-carbethoxy-4-hydroxy-cyclopentano-(h)-quinoline and 7.1 g. methyl iodide were added thereto and the reaction mixture stirred for 7 hours at 100°C. 20 ml. 2N sodium hydroxide solution were then added, a solid material thereby precipitated out. The reaction mixture was heated to 120°C. for 1 hour, cooled and a quantity of water added such that a clear solution was obtained. The small amount of undissolved material was filtered off, the filtrate was treated with activated charcoal, traces of sodium bisulphide were added until the brown color had substantially disappeared and then the mixture was acidified with 5N hydrochloric acid. The carboxylic acid which separated out was filtered off, washed with water, dried and recrystallized from dimethyl sulphoxide. There was obtained 1.65 g. pure 1-methyl-1,4-dihydro-3-carboxy-cyclopentano-(h)-quinolone-(4), which had a melting point of 318°C. (decomp.).

EXAMPLE 37

1-Propyl-1,4-dihydro-3-carboxy-cyclopentano-(g)-quinolone-(4)

1.3 g. 3-carbethoxy-4-hydroxy-cyclopantano-(g)-quinoline, 2.1 g. potassium carbonate, 4.25 g. n-propyl iodide and 12.5 ml. dimethyl formamide were stirred for 2 hours at 100°C. Potassium carbonate was filtered off, the filtrate was evaporated in a vacuum almost to dryness, the evaporation residue was heated under reflux with 24 ml. 2N sodium hydroxide solution for 1 hour and then acidified with 5N hydrochloric acid. The carboxylic acid which precipitated out was filtered off and dried. There were obtained 830 mg. 1-propyl-1,4-dihydro-3-carboxy-cyclopentano-(g)-quinolone-(4). After recrystallization from dimethyl sulphoxide, the product had a melting point of 269°–270°C.

EXAMPLE 38

1-Ethyl-1,4-dihydro-8-nitro-3-carboxy-cyclopentano-(g)-quinolone-(4)

8.2 g. 1-ethyl-1,4-dihydro-3-carboxy-cyclopentano-(g)-quinolone-(4) were dissolved in 40 ml. concentrated sulphuric acid and mixed at 20°–40°C. with 6 ml. 100% nitric acid. The reaction mixture was stirred at ambient temperature for 45 minutes and then poured on to ice. The 1-ethyl-1,4-dihydro-8-nitro-3-carboxy-cyclopentano-(g)-quinolone-(4) which separated out was filtered off and dried, 8.0 g. thereof being obtained, having a melting point of >300°C. The product can be recrystallized from dimethyl formamide.

EXAMPLE 39

1-Methyl-1,4-dihydro-3-carboxy-cyclohexano-(h)-quinolone-(4).

1.84 g. 3-carbethoxy-4-hydroxy-cyclohexano-(h)-quinoline, 4.60 g. potassium carbonate and 10 ml. dimethyl formamide were stirred at 70°C. and 4.57 g. methyl iodide diluted with 10 ml. dimethyl formamide, were added dropwise within the course of 8 hours. The alkylation which took place was followed chromatographically and when the alkylation was still not completed under these conditions, methyl iodide is dimethyl formamide was further added dropwise until the reaction was completed. Subsequently, the reaction mixture was evaporated to dryness in a vacuum, the residue was boiled for 3 hours with 20 ml. 2N sodium hydroxide solution and thereafter acidified with 5N hydrochloric acid. The 1-methyl-1,4-dihydro-3-carboxy-cyclohexano-(h)-quinolone-(4) which separated out was filtered off, dried and recrystallized from dimethyl formamide. There were obtained 1.42 g. of product with a melting point of 258°–260°C.

EXAMPLE 40

1-Ethyl-1,4-dihydro-3-carboxy-8-amino-cyclopentano-(g)-quinolone-(4)

17 g. 1-ethyl-1,4-dihydro-8-nitro-3-carboxy-cyclopentano-(g)-quinolone-(4) were dissolved in 15 ml. concentrated sulphuric acid, 130 ml. glacial acetic acid were added and, with the use of palladium-charcoal, the compound was hydrogenated under normal conditions. After filtering off the catalyst, the reaction mixture was poured on to ice and again filtered. There were obtained 16.1 g. 1-ethyl-1,4-dihydro-3-carboxy-8-amino-cyclopentano-(g)-quinolone-(4) which, after recrystallization from dimethyl formamidedioxan (2:1), had a melting point of 285°–286°C.

EXAMPLE 41

1-Ethyl-3-carboxy-1,4-dihydro-8-acetylamino-cyclopentano-(g)-quinolone-(4)

1.08 g. 1 ethyl-1,4-dihydro-3-carboxy-8-amino-cyclopentano-(g)-quinolone-(4) were heated in 8 ml. acetic anhydride for 45 minutes at 120°C. The reaction mixture was then hot filtered, the filtrate cooled and the crystals which separated were filtered off and recrystallized from dimethyl formamide. There was obtained 0.7 g. 1-ethyl-3-carboxy-1,4-dihydro-8-acetylamino-cyclopentano-(g)-quinolone-(4), which had a melting point of 295°–299°C.

EXAMPLE 42

1-Ethyl-3-carboxy-1,4-dihydro-8-chlorocyclopentano-(g)-quinolone-(4)

1.63 g. 1-ethyl-3-carboxy-1,4-dihydro-8-amino-cyclopentano-(g)-quinolone-(4) were suspended in 16 ml. concentrated hydrochloric acid and 16 ml. water, followed by diazotization at 0°C. with a solution of 414 mg. sodium nitrite in 1 ml. water. The reaction mixture was stirred into a boiling hot solution of 1.2 g. cuprous chloride in 12 ml. water and stirring continued for 10 minutes at 90°C. Subsequently, the reaction mixture was cooled, filtered and the separated 1-ethyl-3-carboxy-1,4-dihydro-8-chlorocyclopentano-(g)-quinolone-(4) was recrystallized from dimethyl formamide.

The yield was 1.2 g. and the product had a melting point of 340°–351°C. (decomp.).

EXAMPLE 43

1-Ethyl-3-carbonyl-1,4-dihydro-6-chlorocyclopentano-(h)-quinolone-(4)

816 mg. 1-ethyl-3-carboxy-1,4-dihydro-6-amino cyclopentano-(h)-quinolone-(4) were suspended in 8 ml. concentrated hydrochloric acid and 8 ml. water and diazotized at 0°C. with a solution of 207 mg. sodium nitrite dissolved in 0.5 ml. water. The reaction mixture was quickly added dropwise to a solution, with a temperature of 90°C., of 600 mg. cuprous chloride in 6 ml. water and thereafter cooled. The separated 1-ethyl-3-carboxy-1,4-dihydro-6-chlorocyclopentano-(h)-quinolone-(4) was filtered off and recrystallized from a mixture of dimethyl formamide and dioxan (1:1). There were obtained 550 mg. of product which had a melting point of 259°–260°C. (decomp.).

EXAMPLE 44

1-Ethyl-3-carboxy-1,4-dihydro-6-formylamino-cyclopentano-(h)-quinolone-(4)

Variant a:

1.36 g. 1-ethyl-3-carboxy-1,4-dihydro-6-amino-cyclopentano-(h)-quinolone-(4) were boiled under reflux in 8.8 ml. of the mixed anhydride of acetic acid and formic acid for 30 minutes. After cooling, precipitation was brought about by the addition of a little ether and the precipitated 1-ethyl-3-carboxyl-1,4-dihydro-6-formylaminocyclopentano-(h)-quinolone-(4) was filtered off and recrystallized from dimethyl sulphoxide. There were obtained 950 mg. of product with a melting point of 277°C. (decomp.).

Variant b:

150 g. technical 3-carbethoxy-4-hydroxy-6-formylamino-cyclopentano-(h)-quinoline, together with 540 g. potassium carbonate, 15 g. potassium iodide and 1.04 liters dimethyl formamide were stirred at 70°C. and 468 g. diethyl sulphate added in about 7–10 portions within the course of 7 hours. The reaction mixture was further stirred for 1 hour at 70°C., inorganic material was filtered off with suction, washed twice with 200–300 ml. hot dimethyl formamide and the combined filtrate and washings evaporated to dryness in a vacuum. The evaporation residue was boiled for 20 minutes in 1.5 liters 2N sodium hydroxide solution and, while still hot, acidified with concentrated hydrochloric acid. After cooling, the reaction mixture was filtered, washed with water and dried. For subsequent formylation, the product was stirred for 15 minutes at 100°C. with 1.07 liters of a mixed anhydride of acetic acid and formic acid, cooled and the precipitated 1-ethyl-3-carboxy-1,4-dihydro-6-formylamino-cyclopentano-(h)-quinolone-(4) filtered off and recrystallized from dimethyl sulphoxide. There were obtained 78.3 g. of product with a melting point of 277°C. (decomp.).

The 3-carbethoxy-4-hydroxy-6-formylamino-cyclopentano-(h)-quinoline used as starting material was prepared in the following manner:

200 g. technical 3-carbethoxy-4-hydroxy-cyclopentano-(h)-quinoline was dissolved in 1 liter concentrated sulphuric acid in such a manner that the temperature did not exceed 40°C. Then, within the course of 1.5 hours, 150 ml. 100% nitric acid were added dropwise at 10°–12°C. When the addition was completed, the reaction mixture was further stirred for 1 hour at ambient temperature, poured on to about 4 kg. ice, filtered off, washed with water and dried. There were obtained 213.9 g. 3-carbethoxy-4-hydroxy-6-nitro-cyclopentano-(h)-quinoline, which had a melting point of 250°–255°C.

200 g. 3-carbethoxy-4-hydroxy-6-nitro-cyclopentano-(h)-quinolone were suspended in 2 liters glacial acetic acid, 80 ml. concentrated sulphuric acid were added, with stirring, and the solution hydrogenated with hydrogen under normal conditions in the presence of palladium-charcoal, the temperature thereby not being allowed to exceed 40°C. When the take up of hydrogen was finished, the catalyst was filtered off, the solution was concentrated to about 600 ml. and poured on to about 2 kg. ice. This was then carefully neutralized with an aqueous solution of ammonia to pH 8, filtered and thoroughly washed with water, with some isopropanol and finally with ether. There were obtained 152 g. of a mixture of 3-carbethoxy-4-hydroxy-6-amino-cyclopentano-(h) quinoline and 3-carboxy-4-hydroxy-6-amino-cyclopentano-(h)-quinoline. The latter was formed by the saponification under the hydrogenation conditions in an amount depending upon the period of hydrogenation and the heat of reaction.

The mixture of 3-carbethoxy-4-hydroxy-6-amino-cyclopentano-(h)-quinoline and 3-carboxy-4-hydroxy-6-amino-cyclopentano-(h)-quinoline was introduced into 1.37 liters of the mixed anhydride of acetic acid and formic acid and heated to 80°C. for 20 minutes, while stirring vigorously. After cooling, the reaction mixture was filtered with suction and washed with glacial acetic acid. There were obtained 165.3 g. of a mixture of 3-carbethoxy-4-hydroxy-6-formylamino-cyclopentano-(h)-quinoline and 3-carboxy-4-hydroxy-6-formylamino-cyclopentano-(h)-quinoline. This crude mixture can be used for the N-ethylation.

EXAMPLE 45

1-Ethyl-3-carboxy-1,4-dihydro-6-propionylamino-cyclopentano-(h)-quinolone-(4)

1.36 g. 1-ethyl-3-carboxy-1,4-dihydro-6-amino-cyclopentano-(h)-quinolone-(4) were suspended in 13 g. propionic acid anhydride and heating under reflux until a clear solution was obtained. The reaction mixture was then cooled, diluted with ether and the crystals which separated out were filtered off with suction. There were obtained 1.15 g. 1-ethyl-3-carboxy-1,4-dihydro-6-propionylamino-cyclopentano-(h)-quinolone-(4) which, after recrystallization from a mixture of dioxan and dimethyl formamide (1:1), had a melting point of 203°–205°C.

EXAMPLE 46

1-Allenyl-3-carboxy-1,4-dihydro-cyclopentano-(h)-quinolone-(4)

900 mg. 1-(pro-2'-yn-1'-yl)-3-carboxy-1,4-dihydrocyclopentano-(h)-quinolone-(4) were stirred for 1.5 hours at 50°C. in 18 ml. 1N sodium hydroxide solution. The reaction mixture was subsequently acidified to a pH of 1–2 with concentrated hydrochloric acid and the precipitated 1-allenyl-3-carboxy-1,4-dihydro-cyclopentano-(h)-quinolone-(4) filtered off and recrystallized from dimethyl formamide. The yield was 630 mg. and the product had a melting point of 213°–214°C.

The 1-(prop-2'yn-1'yl)-3-carboxy-1,4-dihydrocyclopentano-(h)-quinolone-(4) used as starting material, was prepared in the following manner:

1.4 g. 3-carbethoxy-4-hydroxy-cyclopentano-(h)-quinolone and 3.5 g. potassium carbonate were suspended in 10 ml. dimethyl formamide and a mixture of 2.8 g. propargyl chloride and 5 ml. dimethyl formamide added dropwise, with stirring at a temperature of 50°C., within the course of 4 hours. Subsequently, the reaction mixture was further stirred for 2 hours at 50°C., mixed with water and the oil which separated was crystallized by trituration. The crystals were filtered off and boiled under reflux for 2 hours in 15 ml. 2N hydrochloric acid. After cooling, they were filtered off and recrystallized from dimethyl formamide. There were obtained 450 mg. 1-(prop-2'-yn-1'-yl)-3-carboxy-1,4-dihydro-cyclopentano-(h)-quinolone-(4), which had a melting point of 249°–251°C.

EXAMPLE 47

1-Ethyl-3-carboxy-1,4-dihydro-cycloheptano-(g)-quinolone-(4)

1.36 g. 3-carbethoxy-4-hydroxy-cycloheptano-(g)-quinolone, 2.1 g. potassium carbonate, 3.9 g. ethyl iodide and 12.5 ml. dimethyl formamide were stirred for 5 hours at 100°C. The reaction mixture was then evaporated to dryness in a vacuum and the evaporation residue boiled under reflux for 1 hour in 10 ml. 2N sodium hydroxide solution. The reaction mixture was then acidified with 2N hydrochloric acid and the precipitated 1-ethyl-3-carboxy-1,4-dihydrocycloheptano-(g)-quinolone-(4) filtered off with suction and dried. After recrystallization from dimethyl formamide, there were obtained 780 mg. of product, which had a melting point of 251°–253°C.

The 3-carbethoxy-4-hydroxy-cycloheptano-(g)-quinolone used as starting material was prepared in the following manner:

A mixture of 7.5 ml. concentrated sulphuric acid and 4.7 ml. 56 nitric acid was added dropwise, with stirring, at 0°–5°C. to 7.85 g. benzo-cycloheptane. The reaction mixture was stirred for 30 minutes at 0°–5°C., then poured on to ice and extracted with chloroform, the chloroform phase dried over anhydrous sodium sulphate and evaporated. There were obtained 9.7 g. of evaporation residue which was separated in a column of silica gel using ligroin as eluent. There were obtained 3.39 g. pure 8-nitrobenzo-cycloheptane, identified by NMR spectroscopy.

3.3 g. 8-nitrobenzo-cycloheptane, dissolved in 50 ml. methanol, were hydrogenated with hydrogen under normal conditions in the presents of palladium-charcoal or of Raney nickel. There were thus obtained 2.26 g. 8-amino benzo-cycloheptane. This was boiled under reflux with 3.04 g. ethoxy-methylene-malonic acid ethyl ester in 7 ml. benzene for 2 hours and then evaporated to dryness in a vacuum, about 4.95 g. of condensation product remained behind. This was introduced in 15–20 times the amount of diphenyl ether, heated to 250°C., left for 20 minutes at 250°C. and then rapidly cooled. Upon dilution with ligroin, 3-carbethoxy-4-hydroxy-cycloheptano-(g)-quinolone precipitated out and was then filtered off and further worked up. The yield was 2.30 g.

EXAMPLE 48

1-Propyl-1,4-dihydro-3-carboxy-6-formylamino-cyclopentano-(h)-quinolone-(4)

3.16 g. 1-propyl-1,4-dihydro-3-carboxy-6-nitro-cyclopentano-(h)-quinolone-(4) were dissolved in 150 ml. dimethyl formamide and hydrogenated with hydrogen under normal conditions in the presence of Raney nickel. After filtering off the catalyst, the reaction mixture was diluted with water and the precipitated 1-propyl-1,4-dihydro-3-carboxy-6-amino-cyclopantano-(h)-quinolone-(4) filtered off and dried, the yield being 1.4 g. Subsequently, this crude aminocyclopentanoquinolone was boiled for 30 minutes in 13.5 g. of the mixed anhydride of acetic acid and formic acid. After cooling, precipitation was brought about by the addition of ether, the precipitate was filtered off and recrystallized from dimethyl formamide. There were obtained 955 mg. 1-propyl-1,4-dihydro-3-carboxy-6-formylamino-cyclopentano-(h)-quinolone-(4), which had a melting point of 238°–240°C.

The 1-propyl-1,4-dihydro-3-carboxy-6-nitro-cyclopentano-(h)-quinolone-(4) used as starting material was prepared in the following manner:

1.62 g. 1-propyl-1,4-dihydro-3-carboxy-cyclopentano-(h)-quinolone-(4) were dissolved in 7.5 ml. concentrated sulphuric acid and 1.17 ml. 100% nitric acid added dropwise, with ice cooling. After completion of the addition, the reaction mixture was further stirred for 45 minutes at ambient temperature and then poured on to ice. The solid material was filtered off, washed with water and dried. There were obtained 1.9 g. crude 1-propyl-1,4-dihydro-3-carboxy-6-nitro-cyclopentano-(h)-quinolone-(4).

EXAMPLE 49

1-Allyl-3-carboxy-1,4-dihydro-6-amino-cyclopentano-(h)-quinolone-(4)

3.5 g. 3-carboxy-4-hydroxy-6-formylamino-cyclopentano-(h)-quinolone (see Example 24 (b)), 350 mg. potassium iodide, 12.3 g. potassium carbonate, 3,5 ml. water, 35 ml. dimethyl formamide and 7.05 g. allyl bromide were stirred for 2 hours at 70°C., whereafter inorganic material was siltered off with suction and the filtrate evaporated to dryness. The evaporation residue was boiled under reflux in 35 ml. 2N sodium hydroxide solution and 3 ml. dioxan for 10 minutes and subsequently 50 ml. glacial acetic acid were introduced, with stirring, into the hot solution. After cooling, the crystals which separated out were filtered off with suction and recrystallized from dimethyl formamide. There was obtained 1.4 g. 1-allyl-3-carboxy-1-4-dihydro-6-amino-cyclopentano-(h)-quinolone-(4), which had a melting point of 253°–254°C.

EXAMPLE 50

1-Allyl-3-carboxy-1,4-dihydro-6-formylamino-cyclopentano-(h)-quinolone-(4)

1.0 g. 1-allyl-3-carboxy-1,4-dihydro-6-amino-cyclopentano-(h)-quinolone-(4) were boiled under reflux for 10 minutes at 120°C. in 6.4 g. of the mixed anhydride of acetic acid and formic acid. After cooling, the solid material was filtered off and recrystallized from dimethyl formamide. There was obtained 0.95 g. 1-allyl-3-carboxy-1,4-dihydro-6-formylaminocyclopentano-(h)-quinolone-(4), which had a melting point of 250°C.

EXAMPLE 51

Preparation of 1-(Prop-1'-en-1'-yl)-1,4-dihydro-3-carboxy-cyclopentano-(h)-quinol-4-one Variant a:

46 grams 1,4-dihydro-3-carboxy-cyclopentano-(h)-quinol-4-one were suspended in 460 ml. dimethyl formamide, whereafter 165 grams potassium carbonate, 3 grams potassium iodide and 78 grams allyl bromide were added and the reaction mixture then stirred for 2 hours at 100°C. Subsequently, there was again added 48 grams allyl bromide and 1.5 grams potassium iodide, as well as 82.5 grams potassium carbonate, and the reaction mixture further stirred for 4 hours at 100°C. The reaction mixture was then suction filtered, while still hot, to remove inorganic material, the inorganic material was then washed with hot dimethyl formamide and the filtrate, together with the washings, was evaporated to dryness in a vacuum.

The residue from the vacuum evaporation was heated for 5 hours with 600 ml. 5N sodium hydroxide solution and 200 ml. ethanol to 100°C. After cooling, the reaction mixture was acidified with semi-concentrated hydrochloric acid to pH 2 and the carboxylic acid which precipitated out was filtered off. After recrystallization from dimethyl formamide, there were obtained 21.5 grams pure 1-(prop-1'-en-1'-yl)-1,4-dihydro-3-carboxy-cyclopentano-(h)-quinol-4-one, which had a melting point of 207°-210°C.

Variant b:

400 mg. 1-allyl-1,4-dihydro-3-carboxy-cyclopentano-(h)-quinol-carboxy-cyclopentano-(h)-quinol--one were heated under reflux for 5 hours in 6 ml. 5N sodium hydroxide solution and 2 ml. ethanol, whereafter some water was added and the reaction mixture was acidified with 5 N hydrochloric acid. The precipitated 1-(prop-1'-en-1'-yl)-1,4-dihydro-3-carboxy-cyclopentano-(h)-quinol-4-one (380 mg.) was filtered off and dried. After recrystallization from dimethyl formamide, it had a melting point of 207°-210°C.

A better yield and a purer product was obtained (m.p. 200°-202°C.) when, instead of ethanol, ethylene glycol was used as solubilizing agent.

According to the NMR spectrum, the protons of the vinyl groupings were in the cis arrangement.

EXAMPLE 52

Preparation of 1-(Prop-1'-en-1'-yl)-1,4-dihydro-3-carboxy-cyclopentano-(g)-quinol-4-one 1.54 grams 1,4-dihydro-3-carboxy-cyclopentano-(g)-quinol-4-one and 2.97 grams potassium carbonate were suspended in 10 ml. dimethyl formamide. Then, within the course of an hour and while stirring at 70°-80°C., there was added dropwise a mixture of 2.31 grams allyl chloride and 5 ml. dimethyl formamide and the reaction mixture subsequently heated to 100°C. After 2 hours, the reaction mixture was evaporated to dryness in a vacuum and the residue boiled for 5 hours with 15 ml. 5N sodium hydroxide solution and 5 ml. alcohol. It was then diluted with about 15 ml. water and acidified with 5N hydrochloric acid. The precipitated 1-(prop-1'-en-1'-yl)-1,4-dihydro-3-carboxy-cyclopentano-(g)-quinol-4-one was filtered off and dried. The product had a decomposition point of 250°C., after recrystallization from dimethyl formamide, and the yield is 1.18 grams.

EXAMPLE 53

Preparation of 1-Vinyl-1,4-dihydro-3-carboxy-cyclopentano-(h)-quinol-4-one 14.48 grams 3-carbethoxy-4-hydroxy-cyclopentano-(h)-quinoline, 59.2 grams potassium carbonate and 5.64 grams potassium iodide were suspended in 145 ml. dimethyl formamide and, while stirring at 100°-110°C., a mixture of 40 grams 1-chloro-2-methoxy-ethane and 128 ml. dimethyl formamide was added dropwise within the course of 7 hours. Inorganic material was then filtered off with suction, while still hot, the residue was washed with hot dimethyl formamide and the filtrate, together with the washings, was evaporated in a vacuum. The evaporation residue was heated under reflux for half an hour with a mixture of 115 ml. 2N sodium hydroxide solution and 28 ml. dioxan. After cooling, the reaction mixture was acidified with 5N hydrochloric acid to a pH value of 2 and the precipitated carboxylic acid was filtered off and dried. There were obtained 7.0 grams 1-($\beta$-methoxy-ethyl)-1,4-dihydro-3-carboxy-cyclopentano-(h)-quinol-4-one. The compound can be recrystallized from dimethyl sulfoxide and then had a melting point of 222°-226°C.

2.5 grams 1-($\beta$-methoxy-ethyl)-1,4-dihydro-3-carboxy-cyclopentano-(h)-quinol-4-one were heated to 100°-110°C. for 1.25 hours with 25 ml. 48% aqueous hydrobromic acid. The reaction mixture was then introduced into 125 ml. water and the precipitated material was filtered off with suction and dried. There were obtained 2.2 grams of almost pure 1-[$\beta$-hydroxy-ethyl]-1,4-dihydro-3-carboxy-cyclopentano-(h)-quinol-4-one. After recrystallization from a mixture of dioxan and dimethyl formamide, the compound melted at 240°-241°C.

500 mg. 1-[$\beta$-hydroxy-ethyl]-1,4-dihydro-3-carboxy-cyclopentano-(h)-quinol-4-one were heated in 10 ml. nitrobenzene to 140°C. and, simultaneously, gaseous hydrogen chloride was passed through. The progress of the reaction was followed chromatographically. The reaction was finished when no more starting material was found in the chromatogram. The water formed during the halogenation must be continuously removed during the whole course of the reaction (distilling off). When the reaction was finished, the reaction mixture was diluted with about 50 ml. ligroin, a brown oil thereby separated out. The supernatnant ligroin-nitrobenzene solution was decanted off and the remaining oil was triturated with isopropanol and crystallized. There were obtained 310 mg. of almost pure 1-[$\beta$-chloroethyl]-1,4-dihydro-3-carboxy-cyclopentano-(h)-quinol-4-one. After recrystallization from dimethyl formamide/dioxan (3:7), the compound melted at 252° to 253°C.

1 gram 1-[$\beta$-chloroethyl]-1,4-dihydro-3-carboxy-cyclopentano-(h)-quinol-4-one was suspended in 10 ml. anhydrous dioxan and a solution of 920 mg. sodium metal in 20 ml. methanol was added thereto. The reaction mixture was left to stand for 3 hours at ambient temperature, subsequently mixed with 30 ml. water and acidified to pH 2 with 5N hydrochloric acid. The chromatographically pure 1-vinyl-1,4-dihydro-3-carboxycyclopentano-(h)-quinol-4-one which precipitated out was filtered off and dried, the yield being 850 mg. The product can be recrystallized from dimethyl sulfoxide; it then had a decomposition point of 260° to 270°C.

EXAMPLE 54

Preparation of
1-Ethyl-3-carbethoxy-1,4-dihydrocyclopentano(h)-quinolone-(4)

A mixture of 2.57 g 1-ethyl-3-carboxy-1,4-dihydrocyclopentano(h)quinolone-(4), 2.8 g potassium carbonate, 4.5 g ethyl iodide and 25 ml dimethyl formamide were stirred for two hours at 100°C. The reaction mixture was then hot filtered to remove inorganic material and the filtrate diluted with 50 ml water. 2 g 1-ethyl-3-carbethoxy-1,4-dihydrocyclopentano(h)quinolone-(4) thereby precipitated out. This was filtered off and dried. The product can be recrystallized from dioxan; it then has a melting point of 143°–145°C.

EXAMPLE 55

Preparation of
1-Ethyl-3-carbomethoxy-1,4-dihydrocyclopentano(h)-quinolone-(4)

A mixture of 1.3 g 1-ethyl-3-carboxy-1,4-dihydrocyclopentano(h)quinolone-(4), 1.4 g potassium carbonate, 2.1 g methyl iodide and 13 ml dimethyl formamide was stirred for 2 hours at 100°C. The reaction mixture was then hot filtered to remove inorganic material and the filtrate was diluted with 25 ml water. 1.13 g pure 1-ethyl-3-carbomethoxy-1,4-dihydrocyclopentano(h)-quinolone-(4) was obtained; it has a melting point of 135°–137°C.

EXAMPLE 56

Preparation of
1-Ethyl-3-carbopropoxy-1,4-dihydrocyclopentano(h)-quinolone-(4)

A mixture of 1.3 g 1-ethyl-3-carboxy-1,4-dihydrocyclopentano(h)quinolone-(4), 1.4 g potassium carbonate, 2.58 g n-propyl iodide and 13 ml dimethyl formamide was stirred for 2 hours at 100°C. The reaction mixture was then hot filtered to remove inorganic material and the filtrate was mixed with 25 ml water. 1.29 g 1-ethyl-3-carbopropoxy-1,4-dihydrocyclopentano(h)-quinolone-(4) separated out; it has a melting point of 150°–154°C.

EXAMPLE 57

Preparation of
1-[β-Chloroethyl]-3-carbethoxy-1,4-dihydrocyclopentano(h)quinolone-(4)

1.25 g 1-[β-chloroethyl]-3-carboxy-1,4-dihydrocyclopentano(h)quinolone-(4) were suspended in 40 ml anhydrous ethanol and dry hydrogen chloride passed in for about 20 hours, while boiling under reflux. The progress of the reaction was monitored chromatographically. Subsequently, the reaction mixture was cooled and the reaction product precipitated out with cold water. For the separation from non-esterified material, the product was boiled with about 60 ml hot benzene, filtered and the benzene filtrate concentrated, whereby 0.6 g pure 1-[β-chloroethyl]-3-carbethoxy-1,4-dihydrocyclopentano(h)quinolone-(4) precipitated out; it has a melting point of 181°C.

EXAMPLE 58

Preparation of
1-[β-Hydroxyethyl]-3-carbethoxy-1,4-dihydrocyclopentano(h)quinolone-(4)

A mixture of 680 mg 1[β-hydroxyethyl]-3-carboxy-1,4-dihydrocyclopentano(h)quinolone-(4), 700 mg potassium carbonate, 1.13 g ethyl iodide and 7 ml dimethyl formamide was stirred for 2 hours at a bath temperature of 100°C. The reaction mixture was then hot filtered to remove inorganic material and the filtrate diluted with about 15 ml water. 570 mg 1-[β-hydroxyethyl]-3-carbethoxy-1,4-dihydrocyclopentano(h)quinolone-(4) thereby separated out; it has a melting point of 198°–203°C.

EXAMPLE 59

Preparation of
1-[β-Methoxyethyl]-3-carbethoxy-1,4-dihydrocyclopentano(h)quinolone-(4)

A mixture of 770 mg 1-[β-methoxyethyl]-3-carboxy-1,4-dihydrocyclopentano(h)quinolone-(4), 740 mg potassium carbonate, 1.25 g ethyl iodide and 7.7 ml dimethyl formamide was stirred for 2 hours at a bath temperature of 100°C. The reaction mixture was then hot filtered to remove inorganic material and the filtrate was diluted with 20 ml water. 710 mg 1-[β-methoxyethyl]-3-carbethoxy-1,4-dihydrocyclopentano(h)quinolone-(4) thereby precipitated out; it has a melting point of 169°–170°C.

EXAMPLE 60

Preparation of
1-[β-Hydroxyethyl]-3-carbomethoxy-1,4-dihydrocyclopentano(h)quinolone-(4)

A mixture of 2.73 g 1-[β-hydroxyethyl]-3-carboxy-1,4-dihydrocyclopentano(h)quinolone-(4), 2.8 g potassium carbonate, 4.2 g methyl iodide and 14 ml dimethyl formamide was stirred for 2 hours at 100°C. The reaction mixture was then hot filtered from inorganic material and the filtrate was diluted with about 40 ml water. 1.9 g 1-[β-hydroxyethyl]-3-carbomethoxy-1,4-dihydrocyclopentano(h)quinolone-(4) thereby precipitated out. After recrystallizing twice from mixtures of dimethyl formamide and dimethyl sulfoxide, the product has a melting point of 233°C.

EXAMPLE 61

Preparation of
1-[β-Hydroxyethyl]-3-carbobutoxy-1,4-dihydrocyclopentano(h)quinolone-(4)

A mixture of 2.73 g 1-[β-hydroxyethyl]-3-carboxy-1,4-dihydrocyclopentano(h)quinolone-(4), 2.8 g potassium carbonate, 5.5 g n-butyl iodide and 13.6 ml dimethyl formamide was stirred for 2 hours at 100°C. The reaction mixture was then hot filtered to remove inorganic material and the filtrate was diluted with about 40 ml water. 2.15 g 1-[β-hydroxyethyl]-3-carbobutoxy-1,4-dihydrocyclopentano(h)quinolone-(4) precipitated out. After recrystallization twice from aqueous dimethyl formamide, the product has a melting point of 149°C.

EXAMPLE 62

Preparation of
1-[γ-Hydroxypropyl]-3-carbethoxy-1,4-dihydrocyclopentano(h)quinolone-(4)

A mixture of 1.43 g 1-[γ-hydroxypropyl]-3-carboxy-1,4-dihydrocyclopentano(h)quinolone-(4), 1.4 g potassium carbonate, 2.35 g ethyl iodide and 14.3 ml dimethyl formamide were stirred for 2 hours at a bath temperature of 100°C. The reaction mixture was then hot filtered from inorganic material and the filtrate diluted with about 40–50 ml water. 0.9 g 1-[γ-hydroxypropyl]-3-carbethoxy-1,4-dihydrocyclopentano(h)quinolone-(4) thereby precipitated out. After recrystallization from ethanol or dioxan, the product has a melting point of 184°C.

EXAMPLE 63

Preparation of
1-[Prop-1'-en-1'-yl]-3-carbethoxy-1,4-dihydrocyclopentano(h)quinolone-(4)

A mixture of 538 g 1-[prop-1'-en-1-yl]-3-carboxy-1,4-dihydrocyclopentano(h)quinolone-(4), 560 mg potassium carbonate, 936 mg ethyl iodide and 2.8 ml dimethyl formamide was stirred for 2 hours at a bath temperature of 100°C. The reaction mixture was then hot filtered from inorganic material, thereafter washed with some hot dimethyl formamide and the filtrate diluted with about 10 ml water. 500mg 1-[prop-1'-en-1'-yl]-3-carbethoxy-1,4-dihydrocyclopentano(h)quinolone-(4) thereby precipitated out; it has a melting point of 156°–159°C.

EXAMPLE 64

Preparation of
1-Ethyl-3-carbethoxy-1,4-dihydrocyclopentano(h)quinolone-(4)

A mixture of 856 mg 3-carbethoxy-4-hydroxycyclopentano(h)quinoline, 932 mg potassium carbonate, 4.2 ml dimethyl formamide and 1.56 g ethyl iodide was stirred for 2 hours at 100°C. The reaction mixture was then hot filtered from inorganic material and, after cooling, mixed with about 10 ml water, left to stand for 10 minutes and filtered off. The precipitated product (220 mg) was discarded since it was not the desired ethyl ester. The filtrate was diluted with about 20 ml water and left to stand for a day, after which 550 mg 1-ethyl-3-carbethoxy-1,4-dihydrocyclopentano(h)quinolone-(4) precipitated out. According to the chromatogram, the product still contained some starting material. Purification can be carried out by extraction with benzene. The product then has a melting point of 143°–145°C.

By means of the same process, 1-ethyl-3-carbethoxy-1,4-dihydrocyclopentano(h)quinolone-(4) can also be prepared from 3-carboxy-4-hydroxycyclopentano(h)quinolone and correspondingly increased amounts of reagents.

EXAMPLE 65

Preparation of
1-Propyl-3-carbethoxy-1,4-dihydrocyclopentano(h)quinolone-(4)

A mixture of 1.5 g 1-propyl-3-carboxy-1,4-dihydrocyclopentano(h)quinolone-(4), 1.53 g potassium carbonate, 2.59 g ethyl iodide and 7.5 ml dimethyl formamide was stirred for 2 hours at 100°C. The reaction mixture was filtered from inorganic material and the filtrate was mixed with 40 ml water. Pure 1-propyl-3-carbethoxy-1,4-dihydrocyclopentano(h)quinolone-(4) thereby precipitated out. It was filtered off with suction and dried. It has a melting point of 131°–133°C and the yield was 1.56 g.

EXAMPLE 66

Preparation of
1-[β-Acetoxyethyl]-3-carbethoxy-1,4-dihydrocyclopentano(h)quinolone-(4)

1.3 g 1-[β-hydroxyethyl]-3-carbethoxy-1,4-dihydrocyclopentano(h)quinolone-(4) was boiled under reflux for 1 hour with 13 ml acetic anhydride. After cooling, 1-[β-acetoxyethyl]-3-carbethoxy-1,4-dihydrocyclopentano(h)quinolone-(4) crystallized out upon scratching with a glass rod. It was filtered off, washed with ether and dried. The yield was 1.11 g. If desired, the product can also be recrystallized from dimethyl formamide. The product then has a melting point of 196°–198°C.

EXAMPLE 67

Preparation of
1-[β-Methylthioethyl]-3-carbomethoxy-1,4-dihydrocyclopentano(h)quinolone-(4)

A mixture of 100 mg 1-[β-methylthioethyl]-3-carboxy-1,4-dihydrocyclopentano(h)quinolone-(4), 1 ml dimethyl formamide, 141 mg methyl iodide and 91 mg potassium carbonate was stirred for 1 hour at 100°C, subsequently filtered while still hot to remove inorganic material and the filtrate mixed with a little water. Pure-1-[β-methylthioethyl]-3-carbomethoxy-1,4-dihydrocyclopentano(h)-quinolone-(4) thereby precipitated out. It was filtered off, washed with water and dried. The yield was 70 mg and the product has a melting point of 163°–166.5°C.

EXAMPLE 68

Preparation of
1-[β-Methylthioethyl]-3-carbomethoxy-1,4-dihydrocyclopentano(h)quinolone-(4)

20 mg 1-[β-methylthioethyl]-3-carboxy-1,4-dihydrocyclopentano(h)quinolone-(4) were left to stand for 30 minutes at ambient temperature in 1 ml of a mixture of methanol and methylene chloride (1:1) saturated with diazomethane. Thereafter, a further 1 ml of the diazomethane solution was added and the reaction mixture left to stand for a further 30 minutes at 50°C. Subsequently, the reaction mixture was evaporated, triturated with a little methanol and filtered off. There were thus obtained 10 mg 1-[β-methylthioethyl]-3-carbomethoxy-1,4-dihydrocyclopentano(h)quinolone-(4), which has a melting point of 163°–166°C.

According to the same method of working or also analogously to Example 14, from 1-propyl-3-carboxy-1,4-dihydrocyclohexano(h)quinolone-(4), there was prepared 1-propyl-3-carbomethoxy-1,4-dihydrocyclohexano(h)quinolone-(4), which has a melting point of 144°–146°C.

EXAMPLE 69

Preparation of 1-[β-Tosyloxyethyl]-3-carboethoxy-1,4-dihydrocyclopentano(h)quinolone-(4)

A mixture of 500 mg 1-[β-tosyloxyethyl]-3-carboxy-1,4-dihydrocyclopentano(h)quinolone-(4), 5 ml dimethyl formamide, 750 mg ethyl iodide and 375 mg potassium carbonate were stirred for 1.5 hours at 50°C and then filtered to remove inorganic material. The filtrate was mixed with some water and the substance which precipitated was filtered off, washed with water and dried, to give 350 mg of impure product. After recrystallization from dioxan, there were obtained 250 mg pure 1-[β-tosyloxyethyl]-3-carboethoxy-1,4-dihydrocyclopentano(h)quinolone-(4), which has a melting point of 189°C.

The bacteriostatic activity of the compounds in accordance with the invention was evaluated in vitro with respect to the organisms as set out in the following Table.

The absolute bacteriostatic mineral concentration was determined for the following compounds of the invention and for three known or comparison compounds as hereinafter set out.

I — N-(5-nitro-2-furfurylidene)-1-amino-hydantoin (Nitrofurantoin - Norwich)

II — 1-ethyl-1,4-dihydro-7-methyl-4-oxo-1,8-naphthyridine-3-carboxylic acid (Nogram - Winthrop)

III — 1-ethyl-1,4-dihydro-7-methyl-3-carboxy-quinolone (British Pat. No. 830,832)

A — Mixture of 1-ethyl-1,4-dihydro-3-carboxy-cyclopentano(g)- and (h)-quinolone-(4)

B — 1-ethyl-1,4-dihydro-3-carboxy-cyclopentano(g)-quinolone-(4)

C — 1-ethyl-1,4-dihydro-3-carboxy-cyclopentano(h)-quinolone-(4)

D — 1-propyl-1,4-dihydro-3-carboxy-cyclopentano(h)-quinolone-(4)

E — 1-n-butyl-1,4-dihydro-3-carboxy-cyclopentano(h)-quinolone-(4)

F — 1-allyl-1,4-dihydro-3-carboxy-cyclopentano(h)-quinolone-(4)

G — 1-ethyl-1,4-dihydro-3-carboxy-cyclohexano(g)-quinolone-(4)

H — 1-isopropyl-1,4-dihydro-3-carboxy-cyclopentano(g)-quinolone-(4)

I — 1-ethyl-1,4-dihydro-3-carboxy-cyclohexano(h)-quinolone-(4)

J — 1-ethyl-1,4-dihydro-3-carboxy-6-nitro-cyclopentano(h)-quinolone-(4)

K — 1-ethyl-1,4-dihydro-3-carboxy-6-N-acetylamino-cyclopentano(h)-quinolone-(4)

L — 1-ethyl-1,4-dihydro-3-carboxy-8-amino-cyclopentano-(g)-quinolone-(4)

M — 1-ethyl-1,4-dihydro-3-carboxy-8-chloro-cyclopentano-(g)-quinolone-(4)

N — 1-ethyl-1,4-dihydro-3-carboxy-6-chloro-cyclopentano-(h)-quinolone-(4)

O — 1-ethyl-1,4-dihydro-3-carboxy-6-formylaminocyclopentano-(h)-quinolone-(4)

P — 1-allenyl-3-carboxy-1,4-dihydro-cyclopentano-(h)-quinolone-(4)

Q — 1-propyl-1,4-dihydro-3-carboxy-6-formylaminocyclopentano-(h)-quinolone-(4)

R — 1-allyl-3-carboxy-1,4-dihydro-6-amino-cyclopentano-(h)-quinolone-(4)

S — 1-allyl-3-carboxy-1,4-dihydro-6-formylaminocyclopentano-(h)-quinolone-(4)

T — 1-[β-hydroxy-ethyl]-1,4-dihydro-3-carboxy-cyclopentano-(h)-quinolone-(4)

U — 1-[β-methoxyethyl]-1,4-dihydro-3-carboxy-cyclopentano-(h)-quinolone-(4).

V — 1-[β-chloroethyl]-1,4-dihydro-3-carboxy-cyclopentano-(h)-quinolone-(4)

W — 1-[β-(chloroacetoxy)-ethyl]-1,4-dihydro-3-carboxy-cyclopentano-(h)-quinolone-(4)

X — 1-[β-methylmercaptoethyl]-1,4-dihydro-3-carboxy-cyclopentano-(h)-quinolone-(4)

The experiments were carried out in the manner described by W. Vomel, Therapie-Woche, Volume 15, page 1081, 1965. The results are set out in the following Table:

TABLE I

BACTERIOSTATIC ACTIVITY OF CYCLOALKANO-QUINOLONE DERIVATIVES IN VITRO

| ORGANISM | ABSOLUTE BACTERIOSTATIC MINIMAL CONCENTRATION IN µg/ml | | | | | | | | |
|---|---|---|---|---|---|---|---|---|---|
| | I | II | III | A | B | C | D | E | F* |
| Staphylococcus aureus | 8 | 16 | 16 | 2 | 4 | 2 | 2 | 1 | 2 |
| Streptococcus pyogenes | 2 | 64 | 64 | >8 | 16 | 16 | 32 | 16 | >8 |
| Escherichia coli | 4 | 1 | 1 | 0.125 | 2 | 0.125 | 0.25 | 1 | 0.125 |
| Proteus vulgaris | 128 | 1 | 1 | 0.125 | 1 | 0.125 | 0.062 | 0.125 | 0.125 |
| Pseudomonas aeruginosa | >128 | >64 | >128 | >64 | >128 | 32 | >128 | >128 | >15 |

| ORGANISM | ABSOLUTE BACTERIOSTATIC MINIMAL CONCENTRATION IN µg/ml | | | | | | |
|---|---|---|---|---|---|---|---|
| | G | H* | I | J | K* | L | M |
| Staphylococcus aureus | 4 | 4 | 4 | 8 | 1 | 4 | >16 |
| Streptococcus pyogenes | >16 | 16 | 32 | 32 | >8 | 16 | 8 |
| Escherichia coli | 16 | >16 | 0.5 | 1 | 1 | 2 | 2 |
| Proteus vulgaris | 1 | >16 | 1 | 1 | 0.25 | 0,5 | 0.25 |
| Pseudomonas aeruginosa | >64 | >16 | >128 | 128 | >16 | >128 | >16 |

| ORGANISM | ABSOLUTE BACTERIOSTATIC MINIMAL CONCENTRATION IN µg/ml | | | | | | | | | |
|---|---|---|---|---|---|---|---|---|---|---|
| | N | O* | P* | Q | R | S* | T* | U | V | W | X |
| Staphylococcus | | | | | | | | | | |

TABLE I-continued

BACTERIOSTATIC ACTIVITY OF CYCLOALKANO-QUINOLONE DERIVATIVES IN VITRO

| | | | | | | | | | | | |
|---|---|---|---|---|---|---|---|---|---|---|---|
| aureus | 4 | 2 | 2 | 1 | 2 | 4 | 2 | 16 | 2 | 8 | 1 |
| Streptococcus pyogenes | >32 | 8 | 8 | >4 | >4 | >8 | 8 | >4 | 8 | >6 | 4 |
| Escherichia coli | 2 | 0,25 | 0,25 | 0,5 | 0,25 | 0,5 | 0,62 | 0,5 | 0,125 | 0,25 | 0,125 |
| Proteus vulgaris | 1 | 0,125 | 0,125 | 0,125 | 0,25 | 0,25 | 0,125 | 0,5 | 0,031 | 0,25 | 0,032 |
| Pseudonomas aeruginosa | >128 | >16 | >16 | 16 | >256 | >16 | >64 | >64 | 8 | >64 | >16 |

*compound difficulty soluble, experiments begun at 16 μg/ml

In addition, the following compounds were evaluated with respect to their bacteriostatic activity in urine of rats following oral administration. The results of these experiments are set out in Table II which follows:

TABLE II

BACTERIOSTATIC ACTIVITY OF THE URINE OF RATS FOLLOWING ORAL ADMINISTRATION

Bacteriostatic maximum dilution of urine against *Escherichia coli* determined in 50 ml (75 ml) urine samples 22 hours after 20 mg test compound per kg body weight had been orally administered. 6(9) rats were employed for each experiment and every value recorded in the Table represents the results thereby obtained.

| I | II | III | A | B | C | D | E | F | I | J |
|---|---|---|---|---|---|---|---|---|---|---|
| 1:19 | 1:234 | 1:70 | 1:364 | 1:108 | 1:474 | 1:510 | 1:133 | 1:800 | 1:85 | 1:68 |
| K | L | O | Q | T | U | V | W | X | | |
| 1:179 | 1:387 | 1:368 | 1:59 | 1:308 | 1:229 | 1:1040 | 1:316 | 1:252 | | |

The acute oral toxicity was determined in mice. The results are shown in Table III.

TABLE III

| COMPOUND | |
|---|---|
| C | $DL_{50}$ = 4821 mg/kg |
| D | $DL_{50}$ = >2000 mg/kg |
| I[1] | $DL_{50}$ = 250 mg/kg |
| I[2] | $DL_{50}$ = 138 mg/kg |
| II[1] | $DL_{50}$ = 3300 mg/kg |
| II[2] | $DL_{50}$ = 834 mg/kg |

[1]Published value 1964
[2]Unpublished value 1968
[3]Taken from the Nogram (Nalidixinacid)
[4]Unpublished value 1968

As can be seen from Table III, the toxicity of the compounds of the invention is markedly lower than that of Furadantin. The following additional test compounds (illustrative of the invention and two comparison compounds) were employed in the aforesaid experiments.

Compound 1 — 1-[Propen-(1')-yl-(1')]-1,4-dihydro-3-carboxy-cyclopentano-(g)-quinolone-(4)

Compound 2 — 1-[Propen-(1')-yl-(1')]-1,4-dihydro-3-carboxy-cyclopentano-(h)-quinolone-(4)

Compound 3 — 1-Vinyl-1,4-dihydro-3-carboxy-cyclopentano-(h)-quinolone-(4)

Compound A-1 — 1-Ethyl-1,4-dihydro-7-methyl-4-oxo-1,8-naphthyridine-3-carboxylic acid (sold under the trade name "Nogram" by Winthrop Chemical)

Compound B-1 — N-(5-nitro-2-furfurylidene)-1-amino-hydantoin (sold under the trade name "Nitrofurantoin" by Norwich Pharmaceutical Company)

Compounds A-1 and B-1 are comparison compounds) The results are set out in the following Tables.

TABLE 4

BACTERIOSTATIC EFFECTIVENESS IN VITRO

| Bacterium Group | Organism (Strain No.) | Absolute bacteriostatic minimum concentrations in μg/ml for | | | | |
|---|---|---|---|---|---|---|
| | | Compound 1 | Compound 2 | Compound 3 | Compound A-1 | Compound B-1 |
| grampositive organisms | Staphylococcus aureus SG 511 (12) | | 2 | | 32 | 16 |
| | Staphylococcus aureus (103) | 4 | 2 | 8 | 16 | 8 |
| | Streptococcus pyogenes Aronson (75) | | 128 | | >128 | 4 |
| | Streptococcus pyogenes (92) | 8 | 8 | 4 | >32 | 2 |
| | Streptococcus faecalis (155) | | 32 | | >128 | 16 |
| | Streptococcus faecalis (156) | | 16 | | >128 | 16 |
| gramnegative organisms | Escherichia coli (18) | | 0.125 | | 1 | 8 |
| | Escherichia coli (106) | 64 | 0.125 | 0.25 | 1 | 4 |
| | Aerobacter aerogenes (91) | | 0.031 | | 1 | 8 |
| | Aerobacter aerogenes (167) | | 1 | | 4 | 16 |
| | Proteus mirabilis (279) | | 1 | | 4 | 128 |

TABLE 4-continued

BACTERIOSTATIC EFFECTIVENESS IN VITRO

Absolute bacteriostatic minimum concentrations in μg/ml for

| Bacterium Group | Organism (Strain No.) | Compound 1 | Compound 2 | Compound 3 | Compound A-1 | Compound B-1 |
| --- | --- | --- | --- | --- | --- | --- |
| | *Proteus mirabilis* (298) | | 0.125 | | 1 | 128 |
| | *Proteus vulgaris* (206) | 8 | 0.062 | 0.25 | 1 | 128 |
| gramnegative organisms | *Pseudomonas aeruginosa* (71) | | 16 | | >64 | >128 |
| | *Pseudomonas aeruginosa* (164) | | 32 | | >64 | >64 |
| | *Pseudomonas aeruginosa* (195) | >128 | 16 | >16 | >64 | >128 |

TABLE 5

Bacteriostatic Activity of the Urine or Rats Following Oral Administration

Bacteriostatic maximum dilution of urine against *Escherichia coli* (106) determined in 50 ml (75 ml) urine samples 22 hours after 20 mg test compound per kg body weight had been orally administered. 6(9) rats were employed for each experiment and every value recorded in the Table represents the results of each experiment.

| Compound 2 | Compound 3 | Compound A-1 | Compound B-1 |
| --- | --- | --- | --- |
| 1:1100 | 1:182 | 1:234 | 1:54 |
| 1:1200 | 1:180 | 1:280 | 1:30 |
| 1:1120 | 1:208 | 1:270 | 1:41 |
| 1:1000 | | | 1:19 |
| 1:1093 | | | 1:40 |
| | | | 1:21 |

The bacteriostatic activity of additional compounds was measured by determining the absolute bacteriostatic minimum concentration against a number of representative species (see Table 6) and by measuring the excretion of the test compounds in urine and the bacteriostatic effectiveness of the urine after oral administration to rats (see Table 7).

The results are set out in the following Tables.

TABLE 6

Absolute Bacteriostatic Minimum Concentrations in μg/ml

| Test Substance [Prep. Ex. No.] | grampositive organisms | | gramnegative organisms | | |
| --- | --- | --- | --- | --- | --- |
| | *Staphylococcus aureus* | *Streptococcus pyogenes* | *Escherichia coli* | *Proteus vulgaris* | *Pseudomonas aeruginosa* |
| 1-Ethyl-3-carbethoxy-1,4-dihydro-cyclopentano(h)-quinolone-(4) [54] | 128 | 32 | >128 | >128 | >128 |
| 1-Ethyl-3-carbomethoxy-1,4-dihydro-cyclopentano(h)-quinolone-(4) [55] | 64 | 64 | >128 | 128 | >128 |
| 1-Ethyl-3-carbopropoxy-1,4-dihydro-cyclopentano(h)-quinolone-(4) [56] | 32 | 64 | >128 | >128 | >128 |
| 1-[β-Chloroethyl]-3-carbethoxy-1,4-dihydrocyclopentano(h)quinolone-(4) [57] | 64 | 64 | 16 | 16 | >128 |
| 1-[β-Hydroxyethyl]-3-carbethoxy-1,4-dihydrocyclopentano(h)quinolone-(4) [58] | 8 | 8 | >128 | >64 | >64 |
| 1-[β-Methoxyethyl]-3-carbethoxy-1,4-dihydrocyclopentano(h)quinolone-(4) [59] | 2 | >8 | >128 | >64 | >64 |
| 1-(Propyl-3-carbethoxy-1,4-dihydro-cyclopentano(h)quinolone-(4) [65] | >64 | >16 | >128 | >32 | >64 |
| Nalidixic acid (Nogram-Winthrop) | 32 | >32 | 1 | 2 | >64 |
| Furadantin (Nitrofurantoin-Norwich) | 16 | 8 | 4 | 128 | >128 |

TABLE 7

Bacteriostatic Activity of the Urine of Rats Following Oral Administration

Bacteriostatic maximum dilution of urine against *Escherichia coli* (106) determined in 50 ml (75 ml) urine samples 22 hours after 20 mg test compound per kg body weight had been orally administered. 6(9) rats were employed for each experiment and every value recorded in the Table represents the results of each experiment.

| Test Compound | Prep. Ex. No. | Max. Dilution |
| --- | --- | --- |
| 1-Ethyl-3-carbethoxy-1,4-dihydro-cyclopentano(h)-quinolone-(4) | [54] | 1:1392 |
| 1-Ethyl-3-carbomethoxy-1,4-dihydro-cyclopentano(h)-quinolone-(4) | [55] | 1:680 |
| 1-Ethyl-3-carbopropoxy-1,4-dihydro-cyclopentano(h)-quinolone-(4) | [56] | 1:364 |
| 1-[β-Chloroethyl]-3-carbethoxy-1,4-dihydrocyclopentano(h)quinolone-(4) | [57] | 1:3133 |
| 1-[β-Hydroxyethyl]-3-carbethoxy-1,4-dihydrocyclopentano(h)quinolone-(4) | [58] | 1:378 |
| 1-[β-Methoxyethyl]-3-carbethoxy-1,4-dihydrocyclopentano(h)quinolone-(4) | [59] | 1:283 |
| 1-(Propyl-3-carbethoxy-1,4-dihydro- | | |

| Test Compound | Prep. Ex. No. | Max. Dilution |
| --- | --- | --- |
| cyclopentano(h)quinolone-(4) | [65] | 1:693 |
| Nalidic* acid | | 1:234 |
| Furadantin** | | 1:19 |

*Nogram-Winthrop
**Nitrofurantoin-Norwich

The compounds in accordance with the instant invention are anti-microbials and have been found to be bactericidal to the pathogens found in surface infections, gram negative as well as gram positive. They additionally have utility as agents for routine treatment of acute and chronic bacterial infections of the urinary tract, including those caused by Proteus ap. Further they lend themselves because of their properties to use in the prevention of treatment of mixed surface infections of wounds, severe burns, cutaneous ulcers, pyodermas, osteomyelitis, preparation of wounds and burns for skin grafting and prevention of infection of grafts and donor sites.

The compounds of the invention can be employed in the form of aqueous solutions or suspensions thereof, as for instance, in the form of an 0.1 to 10% aqueous suspension or solution; in the form of solutions in non-aqueous, hydroscopic liquid vehicles such as polyethylene glycol, for instance, 0.1–0.5% solutions in polyethylene glycol; incorporation into a water-soluble ointment-like base (concentration 0.1–0.5%) or in a powder base composed for instance of water-soluble polyethylene glycols (concentration 0.1–0.5%); or in a form suitable for ingestion. Thus, a preferred form is a tablet or dragee containing 50–500 mg of active compound. Additionally, the tablet may contain solid carriers as starch, lactose, methylcellulose, talc, highly dispersed silicic acid, high molecular fatty acids, magnesium stearate, gelatine, high molecular polymers, such as polyethylene glycol, and flavoring and color stuffs. Depending on the condition, symptomatic and laboratory responses of the patient 100–1000 mg per day can be administered. Another preferred form for orally administering the compounds of the invention is in the form of a suspension thereof in a water miscible flavored gel. Such a gel can contain from 1 to 100 mg of compound per cc.

It will be understood that the foregoing specification and examples are illustrative but not limitative of the present invention inasmuch as other embodiments within the spirit and scope of the invention will suggest themselves to those skilled in the art.

What is claimed is:

1. A cycloalkano-quinolone compound having the formula:

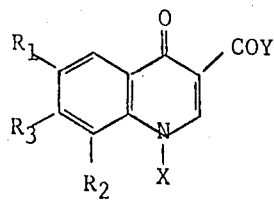

wherein one of $R_1$ and $R_2$ represents a member selected from the group consisting of hydrogen, halogen, nitro, amino and lower alkanoyl amino, and the other of $R_1$ and $R_2$ taken together with $R_3$ forms an alkylene bridge containing 3 to 5 carbon atoms, X is hydrogen or lower alkyl of up to 6 carbon atoms, which may be substituted by a member of the group consisting of halogen, hydroxyl, lower alkanoyloxy, lower alkoxy, phenoxy, benzyloxy, mercapto, lower alkylmercapto, lower carbocyclic arylsulfonyloxy, and lower alkylsulfonyloxy, or X is unsubstituted lower alkenyl including alkadienyl, or lower alkynyl, and Y is a member selected from the group consisting of hydroxyl and lower alkoxy; and the non-toxic salts thereof.

2. Compound as claimed in claim 1 wherein X is hydrogen, lower alkyl or alkenyl.

3. Compound as claimed in claim 1 wherein X is substituted lower alkyl wherein the substituent is selected from the group consisting of halogen, hydroxyl, lower alkanoyloxy, lower alkoxy, phenoxy, benzyloxy, mercapto, lower alkylmercapto, lower carbocyclic arylsulfonyoxy, and lower alkylsulfonyloxy.

4. Compound as claimed in claim 1 wherein X is allenyl.

5. Compound as claimed in claim 1 wherein X is lower alkynyl.

6. Compound as claimed in claim 1 in the form of a pharmaceutically acceptable salt thereof.

7. Compound as claimed in claim 1 wherein said salt is a base salt.

8. N-vinyl-quinolone compound as claimed in claim 1 of the formula:

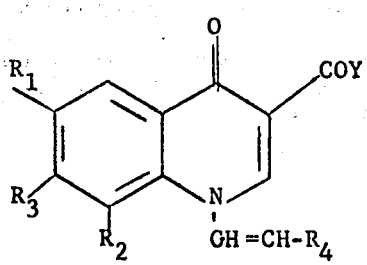

wherein
one of the symbols $R_1$ and $R_2$ is hydrogen and the other one, together with $R_3$, represents a 1,3-propylene bridge;
$R_4$ is hydrogen or lower alkyl; and
Y is hydroxyl, or lower alkoxy;
and the pharmacologically compatible salts thereof.

9. Compound as claimed in claim 8 wherein $R_1$ is hydrogen.

10. Compound as claimed in claim 8 wherein $R_2$ is hydrogen.

11. Compound as claimed in claim 8 wherein $R_4$ is hydrogen.

12. Compound as claimed in claim 8 wherein Y is hydroxyl.

13. Cycloalkanoquinolone-carboxylic acid ester compounds as claimed in claim 1, of the formula

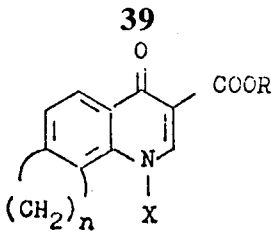

wherein

R is lower alkyl;

X is lower carbocyclic alkyl or substituted lower alkyl wherein the substituent is one member selected from chlorine, hydroxy, lower alkoxy, lower alkanoyloxy, lower alkylthio, lower alkylsulfonyloxy and lower carbocyclic aryl sulfonyloxy; or X is lower alkenyl; and n is 3, 4 or 5.

14. Compound as claimed in claim 13 wherein R is alkyl of from 1 to 5 carbon atoms.

15. Compound as claimed in claim 13 wherein X is alkyl of from 1 to 5 carbon atoms.

16. Compound as claimed in claim 13 wherein X is substituted alkyl of from 1 to 5 carbon atoms, wherein the substituent is chlorine, hydroxy, alkoxy of from 1 to 5 carbon atoms, alkanoyl of from 1 to 5 carbon atoms, or alkylthio of from 1 to 5 carbon atoms.

17. Compound as claimed in claim 13 wherein X is alkenyl of from 1 to 5 carbon atoms.

18. Compound as claimed in claim 1 designated 1-ethyl-1,4-dihydro-3-carboxy-cyclopentano(h)-quinolone-(4).

19. Compound as claimed in claim 1 designated 1-propyl-1,4-dihydro-3-carboxy-cyclopentano(h)-quinolone-(4).

20. Compound as claimed in claim 1 designated 1-allyl-1,4-dihydro-3-carboxy-cyclopentano(h)-quinolone-(4).

21. Compound as claimed in claim 1 designated 1-ethyl-1,4-dihydro-3-carboxy-cyclopentano(g)-quinolone-(4).

22. Compound as claimed in claim 1 designated 1-ethyl-1,4-dihydro-3-carboxy-8-amino-cyclopentano-(g)-quinolone-(4).

23. Compound as claimed in claim 1 designated 1-ethyl-1,4-dihydro-3-carboxy-8-chloro-cyclopentano-(g)-quinolone-(4).

24. Compound as claimed in claim 1 designated 1-ethyl-1,4-dihydro-3-carboxy-6-chloro-cyclopentano-(h)-quinolone-(4).

25. Compound as claimed in claim 1 designated 1-ethyl-1,4-dihydro-3-carboxy-6-formylamino-cyclopentano-(h)-quinolone-(4).

26. Compound as claimed in claim 1 designated 1-allenyl-3-carboxy-1,4-dihydro-cyclopentano-(h)-quinolone-(4).

27. Compound as claimed in claim 1 designated 1-propyl-1,4-dihydro-3-carboxy-6-formylamino-cyclopentano-(h)-quinolone-(4).

28. Compound as claimed in claim 1 designated 1-allyl-3-carboxy-1,4-dihydro-6-amino-cyclopentano-(h)-quinolone-(4).

29. Compound as claimed in claim 1 designated 1-allyl-3-carboxy-1,4-dihydro-6-formylamino-cyclopentano-(h)-quinolone-(4).

30. Compound as claimed in claim 1 designated 1-[propen-(1')-yl-(1')]-1,4-dihydro-3-carboxy-cyclopentano-(h)-quinolone-(4).

31. Compound as claimed in claim 1 designated 1-ethyl-3-carbethoxy-1,4-dihydrocyclopentano(h)quinolone-(4).

32. Compound as claimed in claim 1 designated 1-ethyl-3-carbomethoxy-1,4-dihydrocyclopentano(h)quinolone-(4).

33. Compound as claimed in claim 1 designated 1-ethyl-3-carbopropoxy-1,4-dihydrocyclopentano(h)quinolone-(4).

34. Compound as claimed in claim 1 designated 1-[β-chloroethyl]-3-carbethoxy-1,4-dihydrocyclopentano(h)quinolone-(4).

35. Compound as claimed in claim 1 designated 1-[β-hydroxyethyl]-3-carbethoxy-1,4-dihydrocyclopentano(h)quinolone-(4).

36. Compound as claimed in claim 1 designated 1-[β-methoxyethyl]-3-carbethoxy-1,4-dihydrocyclopentano(h)quinolone-(4).

* * * * *